(12) United States Patent
Mansmann et al.

(10) Patent No.: US 10,485,664 B2
(45) Date of Patent: Nov. 26, 2019

(54) RIGID SEGMENTED FLEXIBLE ANCHORS

(71) Applicant: Formae, Inc., Paoli, PA (US)

(72) Inventors: Kevin A. Mansmann, Paoli, PA (US);
Edward J. Cheal, Duxbury, MA (US)

(73) Assignee: Formae, Inc., Paoli, PA (US)

( * ) Notice: Subject to any disclaimer, the term of this patent is extended or adjusted under 35 U.S.C. 154(b) by 23 days.

(21) Appl. No.: 15/542,352

(22) PCT Filed: Jan. 7, 2016

(86) PCT No.: PCT/US2016/012455
§ 371 (c)(1),
(2) Date: Jul. 7, 2017

(87) PCT Pub. No.: WO2016/112175
PCT Pub. Date: Jul. 14, 2016

(65) Prior Publication Data
US 2018/0271659 A1 Sep. 27, 2018

Related U.S. Application Data

(60) Provisional application No. 62/101,402, filed on Jan. 9, 2015.

(51) Int. Cl.
*A61F 2/30* (2006.01)
(52) U.S. Cl.
CPC ...... *A61F 2/30756* (2013.01); *A61F 2/30767* (2013.01); *A61F 2/30749* (2013.01);
(Continued)

(58) Field of Classification Search
CPC .. A61F 2002/30764; A61F 2002/30761; A61F 2002/30759; A61F 2002/30757;
(Continued)

(56) References Cited

U.S. PATENT DOCUMENTS 4,839,215 A * 6/1989 Starling ............... A61C 8/0012
428/131
5,067,964 A * 11/1991 Richmond .......... A61F 2/30756
623/14.12

(Continued)

FOREIGN PATENT DOCUMENTS

CN 1792350 A 6/2006
CN 1822802 A 8/2006
(Continued)

*Primary Examiner* — Alvin J Stewart
(74) *Attorney, Agent, or Firm* — Volpe and Koenig, P.C.

(57) ABSTRACT

An prosthetic implant replaces hyaline cartilage in a synovial joint with a flexible polymer sliding surface, preferably of hydrogel, on a segmented support with an array of adjacent segments to which the hydrogel is molded. Adjacent segments are laterally and angularly displaceable permitting the implant to conform to rounded or irregular surfaces or to be rolled or folded for arthroscopic placement. Tension cables threaded through segments along a circuit can cinch segments together for stiffening the supporting layer and/or the cable can pull the implant against a bone surface. Adjacent segments can have inter-engaged structures. In some embodiments the segments are carried on a flexible foil or fibrous sheet.

18 Claims, 24 Drawing Sheets

(52) U.S. Cl.
CPC ............... *A61F 2002/3055* (2013.01); *A61F 2002/3092* (2013.01); *A61F 2002/3093* (2013.01); *A61F 2002/30135* (2013.01); *A61F 2002/30136* (2013.01); *A61F 2002/30143* (2013.01); *A61F 2002/30144* (2013.01); *A61F 2002/30235* (2013.01); *A61F 2002/30461* (2013.01); *A61F 2002/30462* (2013.01); *A61F 2002/30471* (2013.01); *A61F 2002/30485* (2013.01); *A61F 2002/30673* (2013.01); *A61F 2002/30757* (2013.01); *A61F 2002/30759* (2013.01); *A61F 2002/30772* (2013.01); *A61F 2002/30841* (2013.01); *A61F 2002/30878* (2013.01); *A61F 2002/30985* (2013.01)

(58) Field of Classification Search
CPC ........ A61F 2/30756; A61F 2002/30754; A61F 2002/30751; A61F 2/30749; A61F 2002/30537; A61F 2002/30538; A61F 2002/3054; A61F 2002/30545; A61F 2002/3055; A61F 2002/30551; A61F 2/3872; A61F 2/3877; A61F 2002/3895; A61F 2/3603; A61F 2/4618; A61B 5/4514
See application file for complete search history.

(56) References Cited

U.S. PATENT DOCUMENTS

| | | | | |
|---|---|---|---|---|
| 5,171,280 A * | 12/1992 | Baumgartner | ........... | A61F 2/441 623/17.12 |
| 5,702,454 A * | 12/1997 | Baumgartner | ........... | A61F 2/441 128/898 |
| 5,755,797 A * | 5/1998 | Baumgartner | ........... | A61F 2/441 623/17.16 |
| 6,387,130 B1 * | 5/2002 | Stone | ................ | A61F 2/4455 623/17.16 |
| 7,351,262 B2 * | 4/2008 | Bindseil | ............ | A61F 2/4455 623/17.11 |
| 7,618,461 B2 * | 11/2009 | Trieu | ................ | A61F 2/441 623/17.11 |
| 8,034,109 B2 * | 10/2011 | Zwirkoski | ........... | A61F 2/4611 606/86 R |
| 8,142,506 B2 | 3/2012 | Huyghe et al. | | |
| 8,206,423 B2 * | 6/2012 | Siegal | ............ | A61B 17/1757 606/279 |
| 8,328,812 B2 * | 12/2012 | Siegal | ........... | A61B 17/320016 606/279 |
| 8,632,591 B2 * | 1/2014 | Vila | ................ | A61F 2/442 623/17.11 |
| 8,673,010 B2 * | 3/2014 | Compton | ........... | A61B 17/7094 623/17.16 |
| 9,017,408 B2 * | 4/2015 | Siegal | ............ | A61F 2/02 623/17.11 |
| 9,095,449 B2 * | 8/2015 | McGuckin, Jr. | ....... | A61B 17/70 |
| 9,168,144 B2 * | 10/2015 | Rivin | ................ | A61F 2/3872 |
| 9,265,611 B2 | 2/2016 | Schwartz et al. | | |
| 9,289,240 B2 * | 3/2016 | Messerli | ............ | A61B 17/68 |
| 9,956,085 B2 * | 5/2018 | Messerli | ............ | A61B 17/68 |
| 2002/0022884 A1 * | 2/2002 | Mansmann | ........... | A61F 2/30965 623/14.12 |
| 2002/0029084 A1 * | 3/2002 | Paul | ................ | A61F 2/28 623/23.63 |
| 2003/0078617 A1 * | 4/2003 | Schwartz | ............ | A61B 17/064 606/230 |
| 2004/0117019 A1 * | 6/2004 | Trieu | ................ | A61F 2/441 623/17.11 |
| 2004/0249463 A1 * | 12/2004 | Bindseil | ............ | A61F 2/28 623/17.16 |
| 2004/0249464 A1 | 12/2004 | Bindseil et al. | | |
| 2005/0043813 A1 * | 2/2005 | Kusanagi | ........... | A61F 2/30756 623/23.58 |
| 2005/0113855 A1 * | 5/2005 | Kennedy, II | ...... | A61B 17/12022 606/185 |
| 2005/0256576 A1 * | 11/2005 | Moskowitz | ............ | A61F 2/441 623/17.12 |
| 2005/0278023 A1 * | 12/2005 | Zwirkoski | .......... | A61B 17/7094 623/11.11 |
| 2006/0041258 A1 * | 2/2006 | Galea | ................ | A61F 2/4455 16/221 |
| 2006/0189999 A1 * | 8/2006 | Zwirkoski | .............. | A61F 2/442 606/90 |
| 2006/0247781 A1 * | 11/2006 | Francis | ................ | A61F 2/442 623/17.16 |
| 2006/0265077 A1 * | 11/2006 | Zwirkoski | .......... | A61B 17/7094 623/17.16 |
| 2006/0271061 A1 * | 11/2006 | Beyar | ............... | A61B 1/00071 606/105 |
| 2006/0293760 A1 * | 12/2006 | DeDeyne | ................ | A61F 2/08 623/23.76 |
| 2007/0233135 A1 * | 10/2007 | Gil | ............... | A61F 2/30756 606/86 R |
| 2007/0233264 A1 * | 10/2007 | Nycz | ................ | A61B 17/1604 623/18.11 |
| 2008/0125863 A1 * | 5/2008 | McKay | ............... | A61F 2/30756 623/11.11 |
| 2008/0133012 A1 * | 6/2008 | McGuckin | ............ | A61F 2/441 623/17.12 |
| 2008/0234827 A1 * | 9/2008 | Schaller | ............ | A61B 17/8852 623/17.16 |
| 2008/0249628 A1 * | 10/2008 | Altarac | ................ | A61F 2/4455 623/17.16 |
| 2008/0249632 A1 * | 10/2008 | Stone | ................ | A61F 2/28 623/23.5 |
| 2009/0076605 A1 | 3/2009 | Linares | | |
| 2010/0331979 A1 * | 12/2010 | McDade | ................ | A61F 2/28 623/14.12 |
| 2012/0123546 A1 * | 5/2012 | Medina | ................ | A61F 2/442 623/17.16 |
| 2012/0283839 A1 | 11/2012 | Strippgen | | |
| 2013/0190873 A1 | 7/2013 | Mansmann | | |
| 2013/0190877 A1 * | 7/2013 | Medina | ............... | A61F 2/4455 623/17.16 |
| 2013/0312897 A1 * | 11/2013 | Vowles | ............... | A61B 17/0401 156/83 |
| 2014/0018918 A1 * | 1/2014 | Wang | ................ | A61F 2/08 623/14.13 |
| 2014/0243993 A1 | 8/2014 | Barrett et al. | | |
| 2014/0277452 A1 * | 9/2014 | Skaer | ................ | A61L 27/227 623/14.12 |
| 2015/0230929 A1 * | 8/2015 | Lorio | ................ | A61F 2/447 623/17.16 |
| 2015/0238318 A1 * | 8/2015 | McCullen | ........... | A61F 2/30756 623/14.12 |
| 2016/0074174 A1 * | 3/2016 | Halverson | ............ | A61F 2/4455 623/17.11 |
| 2017/0007741 A1 * | 1/2017 | D'Lima | ............... | A61L 27/20 |
| 2018/0360610 A1 * | 12/2018 | Patel | ................ | A61F 2/3872 |
| 2019/0008654 A1 * | 1/2019 | Thommen | ............ | A61F 2/4465 |

FOREIGN PATENT DOCUMENTS

| | | |
|---|---|---|
| CN | 102014800 A | 4/2011 |
| WO | 0159068 A2 | 8/2001 |
| WO | 2011156504 A2 | 12/2011 |
| WO | 2014125381 A2 | 8/2014 |

* cited by examiner

107

100

118

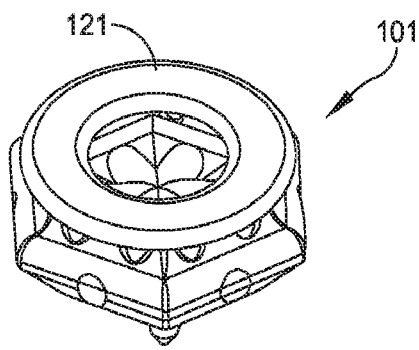
FIG. 25A
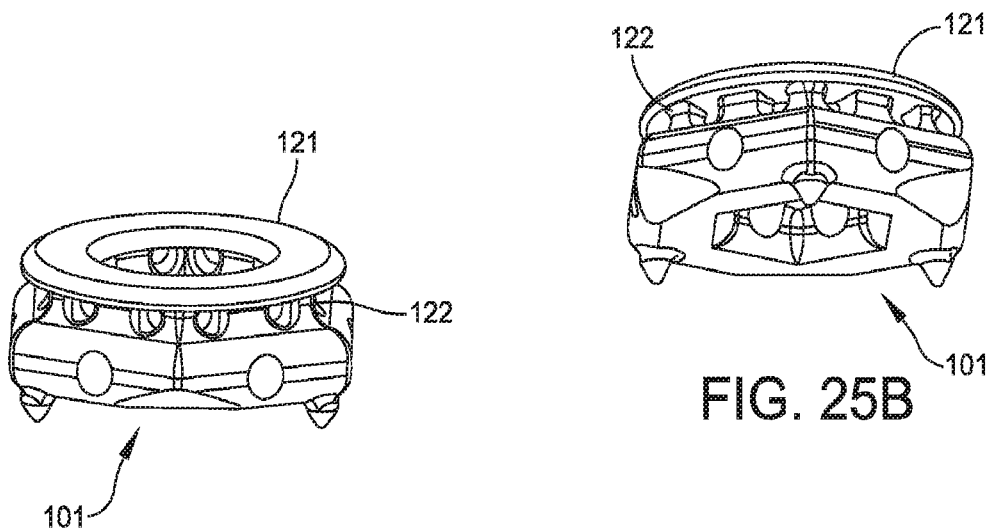
FIG. 25C
FIG. 25B
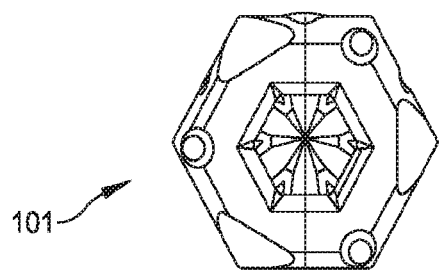
FIG. 25D

⊓ = Staple Anchor
⇧ = Cable
▮ = Bone

RIGID SEGMENTED FLEXIBLE ANCHORS

CROSS REFERENCE TO RELATED APPLICATION

This application is the U.S. National Stage, under 35 U.S.C. § 371, of International Application No. PCT/US2016/012455, filed Jan. 7, 2016, which claims the benefit of U.S. Provisional Application No. 62/101,402, filed on Jan. 9, 2015, the contents of which are hereby incorporated by reference in their entirety.

BACKGROUND

Field of the Invention

This invention concerns prosthetic surgical implants for replacing or supplementing hyaline cartilage in articulating joints. More particularly, implants with plural layers are structured to include laterally adjacent segments permitting relative angular displacement whereby the implant can flex and/or conform to a surface that is curved in orthogonal planes. The opposite faces of the implant have a bone-facing layer on one side, adapted to support tissue ingrowth, and a lubricious hydrogel sliding layer on the opposite side. The segments can be coupled and supported by lines extending through passages (cannulae) in adjacent segments, permitting flexing of the implant along hinging axes. The lines can be anchored and tension on the lines can alter the shape of the implant by application of pressure between segments.

Relevant Art

US Patent Application 2007/0224238, which hereby is incorporated in this disclosure by reference, in its entirety, explains that hyaline cartilage is the main type of cartilage that provides smooth, slippery, lubricated surfaces that slide over and rub against other cartilage surfaces in "articulating" joints, such as knees, hips, shoulders, etc. Natural hyaline cartilage forms as a relatively thin layer (usually no more than about 3 or 4 millimeters thick) that covers certain surfaces of hard bones. While the hyaline cartilage in some joints (such as fingers) is not heavily stressed, the hyaline cartilage in other joints (notably including knees and hips) is frequently and repeatedly subjected to relatively heavy compressive loads, shear forces, and other stresses. Such cartilage does not have a blood supply or cellular structure that enables the type of cell turnover and replacement that occurs in most other tissues. As a result of those and other factors, hyaline cartilage in knees and hips may need repair or prosthetic replacement at fairly high rates among the elderly (due to gradual wear, injury, disorders such as osteoarthritis or rheumatoid arthritis, etc.), and at lower but considerable rates among younger patients (due to injury, congenital joint displacements that lead to unusual wear patterns, etc.).

The present invention relates to certain specific techniques and structural designs for anchoring layers for carrying hydrogel components of implants. Natural hyaline cartilage is present only in relatively thin layers that coat the surfaces of bones and are diffused into the bone tissue for affixation. For emulating hyaline cartilage in an articulating joint, the rigid segmented flexible anchoring layers that carry hydrogel, as disclosed herein, are likewise configured to be thin.

Most hydrogels that have substantial tensile strength (which are the only hydrogels of interest herein) hold water molecules within a cohesive polymeric molecular matrix, in a way that enables migration and diffusion of the water molecules through the molecular matrix. Although such hydrogel materials have at least some degree of deformability for purposes of elasticity, they cannot be in liquid form, i.e., they advantageously return to a specific undeformed shape after loads or stresses have been removed.

In natural cartilage, the hydrogel structure is created by a three-dimensional matrix that is given shape and strength mainly by collagen. Collagen is a fibrous protein that holds together nearly all soft tissues in animals. In synthetic hydrogels, the three-dimensional matrix usually has a molecular structure made of complex polymers that have a combination of: (i) long continuous chains (often called "backbone" chains), containing mainly carbon atoms and sometimes containing oxygen, nitrogen, sulfur, or other atoms as well; (ii) side chains, which branch off the "backbone" chains in ways that can have either regular or semi-random spacing, length, content, etc.; and, (iii) crosslinking bonds, which connect the backbone and side chains to each other in ways that create complex three dimensional molecules that have sufficient spacing between them to allow water molecules to travel within the molecular matrix. In natural cartilage, at the bone cartilage interface there is a zone of cartilage calcification, at the tidal zone, where cartilage is calcified with collagen fibers extending across the tidal zone from the calcified cartilage to the softer cartilage.

Synthetic hydrogel polymers advantageously are hydrophilic, i.e., composed to attract and hold water molecules. This can be accomplished by including large numbers of oxygen atoms (usually in hydroxy groups), nitrogen atoms, or other non-carbon atoms in the backbone and/or side chains, to provide "polar" groups that will attract water, a polar molecule.

Fluid permeability (which involves the ability of water to pass through the molecular matrix of cartilage) is important in the behavior and performance of natural cartilage. As an example, U.S. Pat. No. 6,530,956 (also hereby incorporated by reference) illustrates at FIG. 6 how fluid flow through cartilage can help distribute stresses and pressures that are imposed on cartilage in a load-bearing joint such as a knee, when a person is walking or running.

For the purposes of this invention, synthetic hydrogel polymers are advantageously flexible, and can be rolled into cylindrical forms that can be inserted into a joint that is being surgically repaired, via a minimally invasive incision, using an arthroscopic insertion tube. By avoiding and eliminating the need for "open joint" surgery, arthroscopic insertion of a flexible implant in a rolled-up cylindrical form can spare surrounding tissues and blood vessels from more severe damage during an open joint surgical operation.

Due to these and other factors, hydrogel materials are of interest in joint repair implants, and may be able to provide better performance than the solid plastics, such as ultra-high molecular weight polyethylene ("UHMWPE") that are used today in most hip and knee replacements.

The recent and ongoing efforts to provide improved hydrogel implants for replacing cartilage in joints by Mansmann (the inventor herein) are described in U.S. Pat. No. 6,629,997 ("Meniscus-type implant with hydrogel surface reinforced by three-dimensional mesh") and published applications US 2002-0173855 ("Cartilage repair implant with soft bearing surface and flexible anchoring device"), US 2002-0183845 ("Multi-perforated non-planar device for anchoring cartilage implants and high-gradient interfaces"), US 2004-0133275 ("Implants for replacing cartilage, with negatively-charged hydrogel surfaces and flexible matrix reinforcement"), all of which are hereby incorporated by reference, as though fully set forth herein.

A bone surface that is covered by a layer of hyaline cartilage is referred to herein as a "condyle." However, it should be noted that this term is not always used consistently, by physicians and researchers. Some users limit "condyles" to the rounded ends of elongated bones. This usage includes the long bones in the arms and legs; it usually but not always includes smaller elongated bones in the hands, fingers, feet, and toes; and it normally excludes the cartilage-covered "sockets" in the ball-and-socket joints of the hips and shoulders (while encompassing the complementary ball ends of the other bone that fits such a socket). By contrast, other authors use "condyle" to refer to any bone surface covered by hyaline cartilage, including the socket surfaces in hip and shoulder joints. Since reinforced hydrogels as disclosed herein can be used to replace hyaline cartilage segments on any bone surface, the broader definition (which covers any bone surface covered by hyaline cartilage, including long bones, finger joints, socket surfaces in hips and shoulders, etc.) is used herein unless specifically excluded in the description or its context.

A condylar surface (i.e., a hyaline cartilage-carrying bone surface) contains a transition zone, called the subchondral layer or zone, at the interface between the hard bone and the cartilage. This transition zone strengthens and reinforces the cartilage, ensuring that the cartilage (which is relatively soft) is not readily pushed or scraped off the supporting bone when a joint is subjected to loading and shearing stresses. In the transition zone, large numbers of microscopic collagen fibers, firmly anchored in the hard bone, emerge from the bone in an orientation that is generally perpendicular to the bone surface at that location.

When rounded surfaces are involved, a direction normal to the surface may be called radial; the surface-parallel direction at any point on a rounded surface is called tangential. For convenience, the descriptions and drawings herein typically assume a cross section wherein a bone surface is positioned horizontally, with a layer of cartilage resting above it and on top of it, and with the smooth articulating surface of the cartilage as the upper exposed surface of the structure. This orientation is for convenience of description, often with reference to an illustration. Unless otherwise stated, adjectives such as up/down, over/under, above/below and similar limitations should be taken as referring to an arrangement wherein the bone is assumed to be the base or lower tissue unless otherwise described, or according to a depiction in the drawings, and should not be regarded as limiting features of the subject invention. The joint might be oriented in any direction at a given time.

Bone is a relatively rigid biological material compared to cartilage. There are different typical rigidities of bones in the functional skeleton, corresponding to a large extent to the mechanical demands of the segment of bone, as outlined by Wolff's Law. Subchondral bone, the bone directly adherent to a cartilage layer at the joint surface, is comprised of a thin dense layer of bone. Less dense woven bone supports the subchondral joint articular surface. Dense cortical bone is found in the long bones for structural support.

To employ soft hydrogel in an implant to replace damaged cartilage, it is advantageous to anchor the hydrogel to the associated bone articulating surface in such a way as to promote healing of the hydrogel implant to the bone recipient site, i.e., to secure the implant that carries the hydrogel surface exposed for sliding articulation. There is a significant modulus of elasticity mismatch in structural characteristics between the cartilage, with relatively soft fragile material properties, and the subchondral bone, with relatively tough rigid material properties. This material modulus mismatch is well known. See, e.g., Rockwood & Green's Fractures in Adults, 6th Edition, 2006 Lippincott Williams & Wilkins.

SUMMARY

The present developments concern continuing work based upon mechanical, tribological and pilot animal data, to develop hydrogel-based therapeutic devices and techniques that improve treatment options available for progressive osteoarthritis (OA) and post-traumatic osteoarthritis (PTOA). An object is to repair irreversibly damaged articular bearing surfaces so as to improve function and reduce the progression, pain, suffering, care and expenses associated with arthritis.

OA/PTOA can impact any joint, with variable disability impact. Although PTOA differs from OA in etiology, age of onset, associated pathologies and index injury treatment focus, both conditions can result in extensive damage to articular cartilage. Once damage to articular cartilage occurs, conservative management (e.g., anti-inflammatory drugs, braces and visco-supplementation) has only marginal temporizing, palliative success. There are currently no successful, minimally invasive interventions in use for early end stage, bone on bone, joint pathologies that predictably forestall or possibly wholly avert the need for total joint replacement (TJR) or joint arthrodesis (JA). Conventionally, TJR is the definitive procedure for OA/PTOA of the hip, knee and shoulder while joint fusion (JA) is an acceptable alternative for smaller synovial joints and as salvage, last resort alternative for complications of the shoulder, hip or knee. Though a very successful procedure, TJR is associated with an open surgical approach, complete replacement of the natural joint, and typically requires a significant hospitalization with post-surgery rehabilitation.

It would be quite advantageous to provide "pre-arthroplasty" interventions that do not require an open joint approach, extensive hospitalization and prolonged recovery and rehabilitation times, for both military and public needs. It is an object of the present disclosure to prosthetically resurface synovial bone-on-bone synovial joints, using structurally supported hydrogel configured for attachment to a bone by arthroscopic techniques. More generally, the invention seeks to correct cartilage pathologies before progressive bone erosion causes joint deformities indicating that more drastic treatment is necessary.

This disclosure concerns improved anchoring systems joint for replacing damaged cartilage in synovial joints. These implants are flexible, due to segmentation of the implants for delivery into the joint. In addition these devices are designed with an integral cable to be tensioned and thereby compressing the individual rigid segments together, to restore rigidity as the implant is installed and fixed to bone. The indications for use centers around the treatment of painful osteoarthritic synovial joints, for instance with bone on bone pathology secondary to damaged cartilage. These devices are designed for installation through an arthrotomy, arthroscopically assisted mini-arthrotomy or arthroscopy.

According to the present disclosure, a flexible conforming medical device, is structured with laterally adjacent coupled segments, enabling the device to be folded or rolled and delivered into an arthritic joint through a minimal incision. The device can be opened on the joint surface with a lubricious hydrogel material on one side facing toward the opposed bone. The opposite side can be configured for bone ingrowth and/or to be anchored using fasteners. The segments form a flexible sheet structure.

In certain embodiments, the segments are connected to one another using aligned passageways receiving tensioning lines or cables. The aligned passageways can include edge mounted interlocking hinge parts on adjacent segments such that the adjacent segments can flex around an axis defined by the line or cable extending through the passageways.

In certain embodiments the flexing around axes defined by parallel spaced tension lines is configured to permit the implant to be folded or rolled into a tube for delivery through a small incision in an arthroscopic procedure. Upon introduction, the implant is placed at the required site. In certain embodiments, tension applied to the lines or cables can draw together the segments due to the path of lines or cables around a circuit or otherwise between end points at which the line or cable can be terminated at a connection to a segment or by anchoring to a fastener embedded in bone.

An array of segments can be coupled by membranes, foil, hinges or cables in respective embodiments, and can be delivered and secured to the boney recipient site, thereafter contributing implant rigidity for good functional performance, a stabilization in position for tissue healing and potential tissue ingrowth.

These and other objects are achieved in an implant for replacing hyaline cartilage in a synovial joint, the implant having a flexible polymer sliding surface, preferably of hydrogel, on a supporting layer that is segmented. More particularly, the supporting layer has an array of laterally adjacent rigid segments to which the hydrogel is molded. The segments are displaceable at least angularly relative to one another, such that the implant can flexibly conform to rounded or irregular surfaces. The implant can be rolled up or folded for arthroscopic introduction into the joint, after which the implant is placed and anchored to associated bone. The segments can be regular polygons, for example. Alternatively, the implant can be segmented in a manner that is customized to the topography of the bone surface, for example with junctions between segments aligned perpendicular to curvature gradients such that the implant can rest against rounded surfaces especially including the condoyles at the ends of articulating bones.

In some embodiments, cables are threaded through the segments and facilitate anchoring to a bone. Tension applied to a cable extending around a circuit and intersecting plural segments can pull the intersected segments together or cinch the encircled segments together, for stiffening the supporting layer. The cable can be anchored at fasteners along the circuit and also anchored at end points that are beyond edges of an implant wrapped over a rounded bone surface such that tension pulls the segments of the implant down against the rounded surface. Adjacent segments can have complementary nesting shapes that hold a relative orientation when the segments are pulled into abutment, such as relatively inclined surfaces.

In certain embodiments, the segments are discrete elements but are affixed to one another in a flexible or hinging manner where adjacent segments abut. In an embodiment using cables, adjacent segments can have inter-engaged hinge knuckles such that a cable through the knuckles functions as a hinge pin as well as an anchoring or tensioning element. This cable can be routed so as to provide hinging lines along which the segments are flexibly inclined relative to a flat plane to wrap over a curvature.

An object of this invention is to provide improved methods of stable secure fixation of a soft polymer or hydrogel bearing surface to a relatively rigid bone recipient site establishing a modulus of elasticity gradient from the rigid bone to the compliant bearing surface, resulting in a stable replacement device for damaged cartilage in an arthritic joint.

Another object is to provide a practical method of dividing a rigid structure into plural individual rigid segments, thereby creating a flexible device to facilitate the delivery of the device through a minimal opening, to the desired site of function.

A further object is to achieve a method to restore these flexibly associated individually rigid segments into a rigid whole device, in particular by applying tension via a tensioning line that draws the segments into lateral abutment.

In certain embodiments, the implants are arbitrarily sized and comprise an array of regularly shaped segments from which a required anatomical shape is approximated and cut out. In other embodiments, an implant that is shaped to accommodate the installation site is subdivided to form segments that can be angularly diverted from one another and arranged loosely or drawn laterally together. An anatomically shaped implant thus can be subdivided by strategic serpentine cutting into plural segments, along lines at which the rigid segments are hinged together permitting the device to be flexed. Flexing can allow the implant to the rolled or folded for delivery into the joint and then opened and restored to full size. The subdividing lines between segments advantageously complement the contour of the installation site, for example with dividing lines oriented perpendicular to surface curvature gradients, such that the segmented implant fits closely against the surface. As so fitted, implant rigidity is then achieved by tensioning of one or more cables traversing the implant, during the installation anchoring procedures.

Another object of the invention is to provide a flexible sandwich honeycomb segmented structure that can be flexed and delivered through a small opening and then restored to its larger functional geometric shape and internally tensioned into a rigid honeycomb structure.

Among other embodiments, a flexible sheet is provided as a carrier of the segments, for example comprising a woven or nonwoven fiber or a flexible thin metallic foil as a binding membrane on one side of the rigid segments, thereby controlling the alignment, orientation and configuration of the implant in a flexible state and the accommodating movement into a final, tensioned, compressed rigid state of the device.

A method for securing an implant employs quilted mesh, having increased loft for compression, by a tensioned suture grid, to relieve tension stress at the polymer mesh interface of a relatively soft polymer or hydrogel bearing surface to a relatively rigid bone recipient site for replacement of damaged cartilage in an arthritic joint.

These and other objects of the invention will become more apparent through the following summary, drawings, and description of the preferred embodiments.

BRIEF DESCRIPTION OF THE DRAWINGS

The appended drawings illustrate certain nonlimiting embodiments for demonstrating aspects of the invention, and wherein:

FIG. 25A-D are perspective and plan views of an alternative embodiment of a rigid segment for use in an array, in particular having a domed top with lateral macro-pores into which hydrogel protrudes in a composite molding.

FIG. 29A shows affixation of a rigid-segment array to the backer sheet; whereas

DETAILED DESCRIPTION OF EXEMPLARY EMBODIMENTS

According to the invention, sheet-like prosthetic implants replace cartilage in articulating joints, namely joints wherein synovial fluid lubricates the relative sliding of surfaces on articulating bones, which surfaces are arranged to slide over one another. Such joints are found in the limbs of mammals such as the knees and shoulders of humans, and are distinct from joints that do not involve sliding surfaces such as intervertebral joints.

Figure 1A:
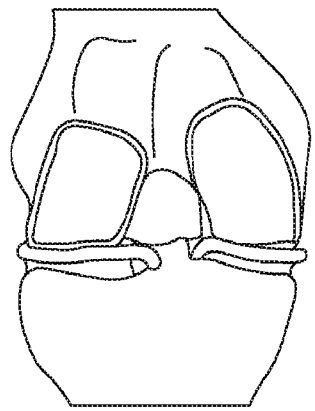
FIGS. 1A and 1B are the anterior and lateral views of a human knee model showing articulating ends of the femur and tibia with hydrogel implants supplementing or supplanting medial and lateral articular cartilage at the tibial plateau, the femoral condoyles and the menisci.
Figure 1B:
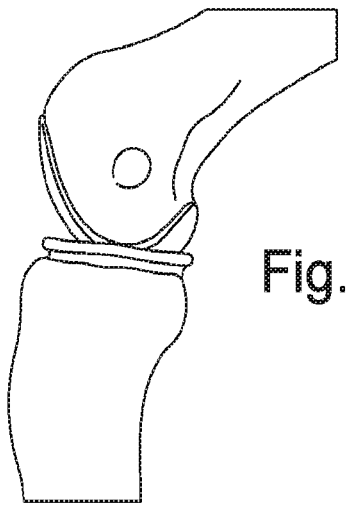

In the illustration of the internal elements of the human knee shown in FIGS. 1A, 1B, the bones articulate such that as the femur and tibia become inclined relative to one another at different angles, the hyaline cartilage that naturally occurs on the ends of these bones, namely on the medial and lateral condoyles at the end of the femur and at the top of the tibia, slide relative to one another and relative to the meniscus, an intervening portion of cartilage that also bears compression while facilitating sliding contact.

It is an aspect of this disclosure that prosthetic implants are provided to wholly or partly replace the natural cartilage elements, and the prosthetic elements comprise sheets configured as adjacent segments.

The segments are displaceable relative to one another in certain ways described herein for conforming to the topography where the segments are deployed, such as to wrap over a convex bone surface or to fit into a concavity.

The segments carry a hydrogel lubricious sliding layer on at least one side. In the case of the femoral and tibial cartilage implants that emulate hyaline cartilage natural ingrown with the bone surface, the opposite side from the hydrogel has aspects that facilitate affixation to the bone surface, preferably including anchoring and optionally configured to encourage tissue ingrowth. In the case of the meniscal cartilage implants that emulate a meniscus that naturally is attached to adjacent tissues in the joint capsule, both sides of the implant carry hydrogel lubricious sliding layers. Supporting structures such as a reinforcing rib can wrap around each meniscal implant to ends that are anchored in the tibia to keep the implant stationary between the femur and tibia.

Figure 2A:
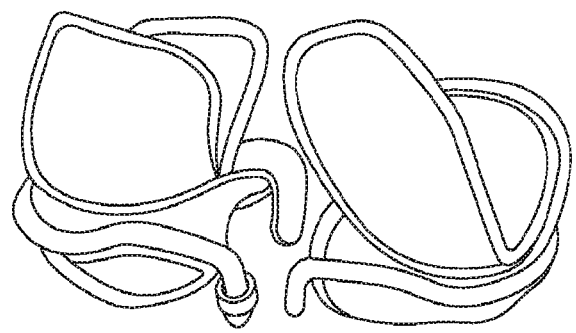
FIGS. 2A, 2B and 2C are views from different perspectives showing the implants seen in FIG. 1A apart from the associated bones.
Figure 2B:
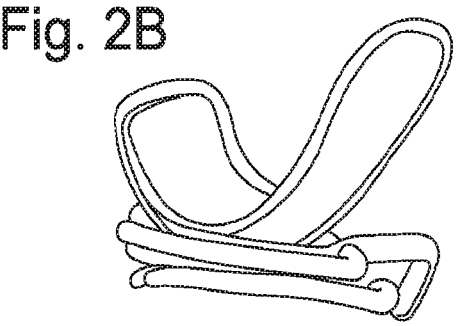
Figure 2C:
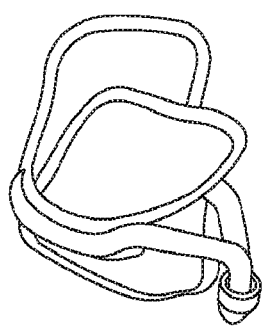

FIGS. 1A, 1B show a knee joint with hyaline and meniscal cartilage implants in place, in anterior and lateral side elevation views. FIG. 2A shows the implant cartilage configurations separately from the bones. FIGS. 2B, 2C show the implant cartilage elements for one condoyle from different orientations. It is apparent in these views that the implants are generally sheet-like but the sheet curves over rounded bone surfaces. The implants cover the contour of curved bone surfaces that anatomically are capable of coming into sliding contact with the opposed bone at some position within the range of articulation of the joint.

According to the present disclosure, at least the implants elements that cover curved condoyle surfaces are segmented. Segmentation of the implants into discrete segments or flexibly-coupled segments allows relative displacement between adjacent segments as needed for the implant to conform to a curved bone surface contour. An array of associated segments can be dimensioned to fit within the required perimeter. The segments can be regular geometric shapes or shapes that are selected as discrete zones of an implant with an irregular rounded shape, that fits the necessary perimeter. The abutting edges between the segments advantageously can be aligned with changes in the gradient of curves of the bone surface contour, such that segments on either side of the change lay flat against the bone surface.

Figure 3A:
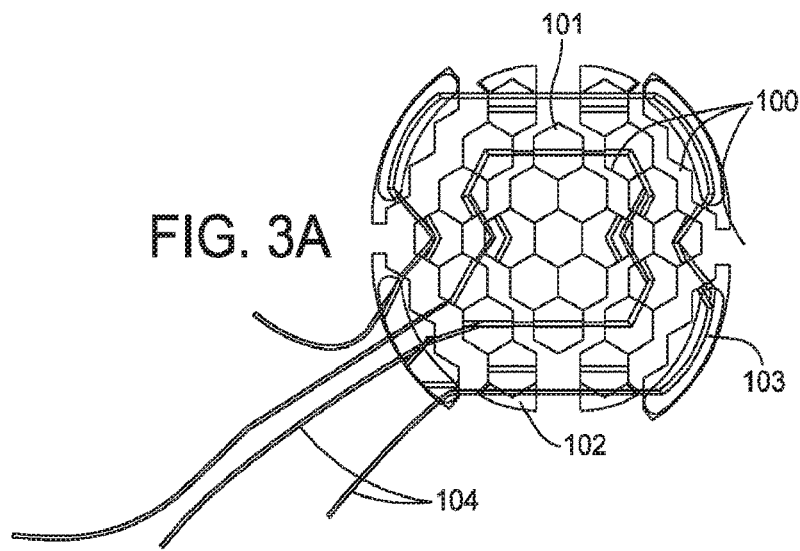
FIG. 3A is a plan view showing a structurally supportive component that can be provided in an implant, wherein certain segments (shown as hexagons) are joined to other segments at lines of lateral abutment, and groups of joined segments provide pathways in which tensioning cables are provided for drawing the groups of segments inwardly.
Figure 3B:
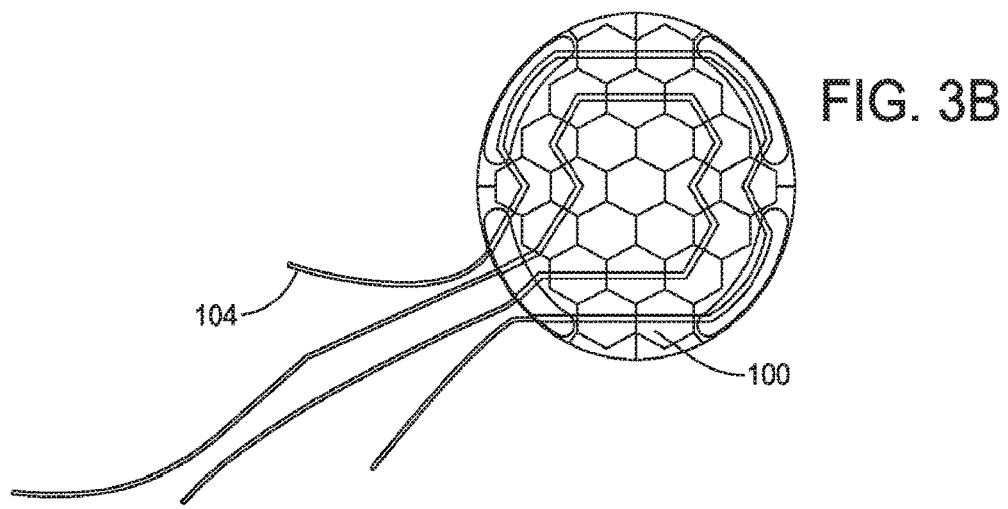
FIG. 3B is a perspective view corresponding to FIG. 3A wherein the groups of segments are drawn inwardly into lateral abutment in a flat plane.
Figure 3C:
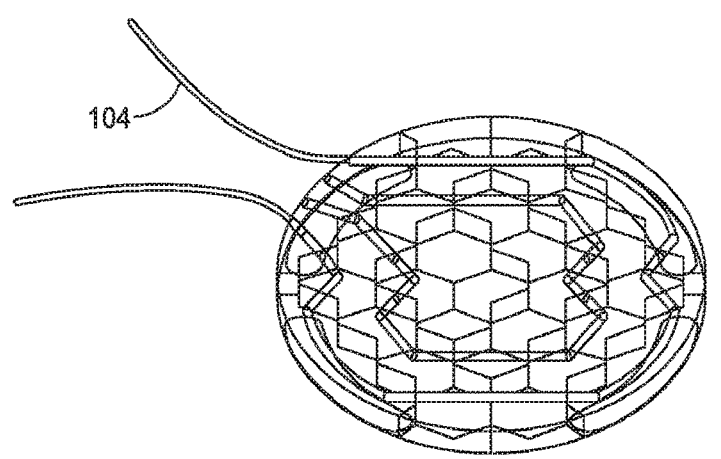
FIG. 3C is another perspective view of the component of FIG. 3B with the segments drawn inwardly into lateral abutment.

FIGS. 3A-3C demonstrate the segmentation of an implant using disc-like segments that are of regular shape, such as hexagons. In some embodiments discussed below, each hexagon or other segment can be a discrete separable element, optionally affixed by one of several alternatives to its adjacent hexagons or other shaped segments. As shown in FIG. 3A, several grouped subsets of hexagons together encompass a given perimeter shape, in this example a circle. In FIG. 3A, the hexagonal segments 100 are grouped into a central subset 101, two arcs 102 that bracket the central subset, and several rim elements 103. The segments within each subset can be affixed to one another in a manner that allows the segments to flex angularly relative to one another. In this embodiment, the grouped-segment subsets are laterally displaceable for the other subsets. Therefore, individual hexagon segments can flex to conform to a curve, and grouped segment subsets can be moved relative toward and away from one another. FIG. 3A shows grouped subsets that are laterally spaced while occupying a plane. FIGS. 3A-3C demonstrate that by providing one or more tension lines 104 that intersect the segments or grouped segment subsets, the array is physically tethered and can be drawn inwardly into lateral abutment by applying tension to the lines 104 that intersect the segments or their grouped subsets.

In FIGS. 3A-3C, the implant assumes a relatively rigid shape in a plane due to lateral abutment of tile-like segments 100 in regular polygonal shapes. In FIG. 3A, plural tile-like segments are coupled into subsets 101, 102, 103 that form distinct zones of an area to be encompassed. The segments are joined by tension cables 104 extending through holes in the segments and extending between segments, advantageously extending between segments that are members of different subsets and zones. As also shown in FIGS. 3B and 3C, when one or more such cables is tensioned, gaps between segments are closed. The lateral abutment of the segments in tension provides a structure with some rigidity because the segments 100 are complementary to one another, such as regular hexagons.

According to one embodiment, an implant as in FIGS. 3A-3C is assembled from repetitive polygon structures for lateral nesting compression into a solid relatively rigid structure, coupled with arbitrary additional elements such as perimeter elements that are rounded or otherwise anatomically shaped for definition of the functional edges, corners and anatomic surfaces that emulate natural cartilage. The embodiments of FIGS. 3A-3C illustrate the segments being brought into lateral abutment in a plane (i.e., a substantially flat shape). By a suitable selection of lateral relatively displaceable segments and perimeter or array-internal grouped subsets, the implant can be adapted to a given articulating joint and prosthetic restoration, including various curved surfaces.

Figure 4A:
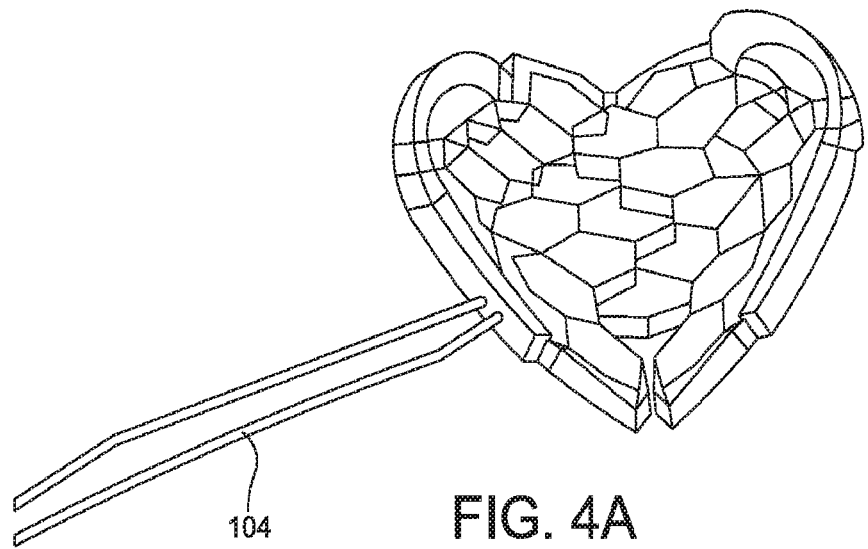
FIGS. 4A and 4B are respectively perspective and elevation views showing an embodiment as in FIG. 3B except that bilateral groups of the segments are pulled by the tension lines to hinge, pulling the bilateral groups into an alternative cup shaped contour.
Figure 4B:
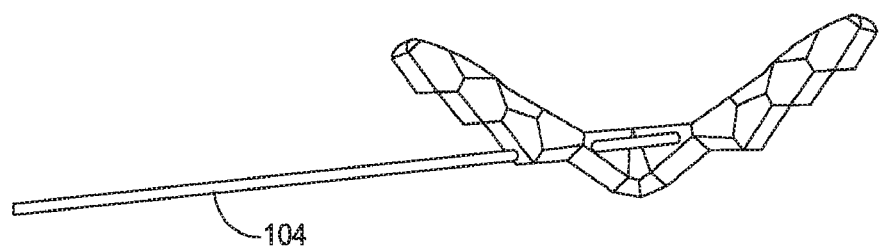

FIGS. 4A through 4C are perspective views of a segmented rigid structure with cables binding the segments together, resulting in a controllably flexible construct that can assume a non-planar shape due to the interaction of the segments and tensioning cables 104. The implant is flexible when the binding cable is not under tension. When tensioned, the flexible rigid segmented structure loses its flexibility due to cable tension causing compressive abutment of the segments. However in these embodiments, the segments are coupled in that manner that permits the implant to assume a nonplanar shape. Specifically, the tension lines include at least one outer circuit that, when tensioned sufficiently, pull the segments along the outer circuit up from the plane of segments inside the outer circuit.

In FIG. 4A, there are two tensions cable circuits, one surrounding the other. By applying tension to the cables beyond the minimum tension that brings segments 100 into lateral abutment, the shape of the implant can be flexed into a cupped or dished curve. Tension applied specifically to laterally outer segments surrounding a planar center causes the outer segments to become inclined relative to the planar center. The outer segments can be lifted from the plane of the center and caused to overlap inner segments, as shown in FIG. 4A. Alternatively, the subsets can meet at hinging lines that extend across the implant. FIGS. 4B and 4C demonstrate drawing an implant into a generally cupped shape by flexing subsets 102 and 103 relative to a planar central subset 101.

In the case of plural outer and inner tension circuits, for example as shown in FIGS. 3A, 3B, tension can be applied to the respective tension circuits to differing extents, producing a greater angular deflection in one circuit and less in another. Likewise, the direction of angular deflection can be varied, for example to configure an implant with a planar center, and upwardly deflected inner annulus and a downwardly deflected rim, following an irregular curve of the bone surface and enabling the implant to rest closely against the bone surface. In order to achieve a curve or to provide a change in deflection from upward to downward, the laterally abutting faces of the segments or subsets can be inclined at an edge plane angle that is other than perpendicular to the plane of the segments or subsets. In that case pulling the segments into abutment causes the abutting segments or subsets to become relatively inclined according their edge plane angles.

One advantage of subdividing the implant into relatively movable segments that can become inclined to one another along hinging lines or the like is that the implant can be folded or rolled into a small volume, introduced into the articulating joint through a small incision, especially using by arthroscopic surgical tools, and opened in place on a prepared bone surface. At that point, tension on cables traversing the segments is used to draw the implant into a predetermined shape, or at least to pull the implant down against the surface of the bone by applying tension between anchoring points.

Figure 5A:
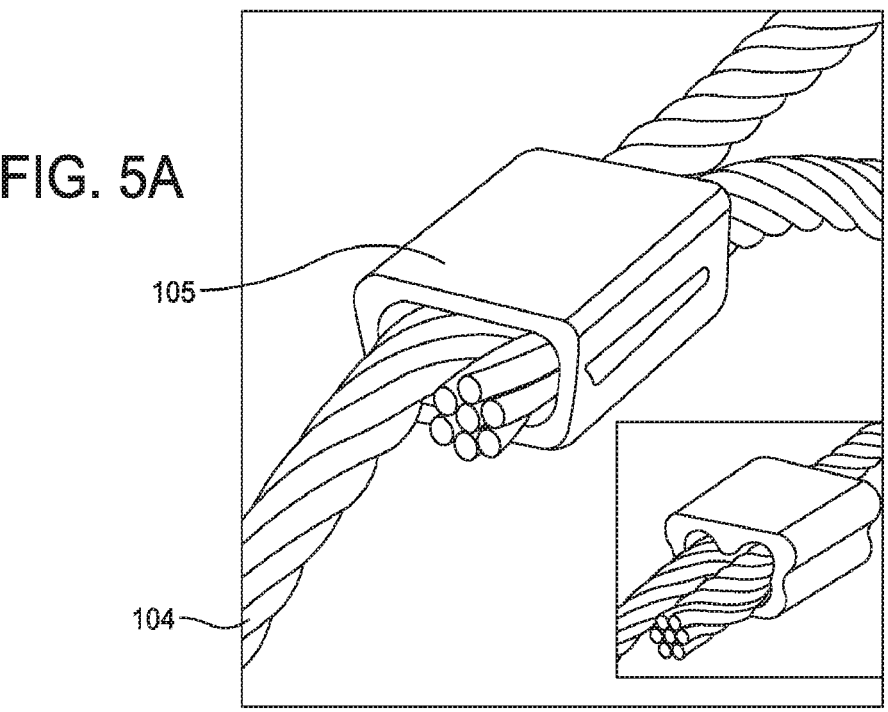
FIGS. 5A and 5B are examples of orthopedic cerclage cable crimp and fixation devices of a type useful to affix tension cables as described.
Figure 5B:
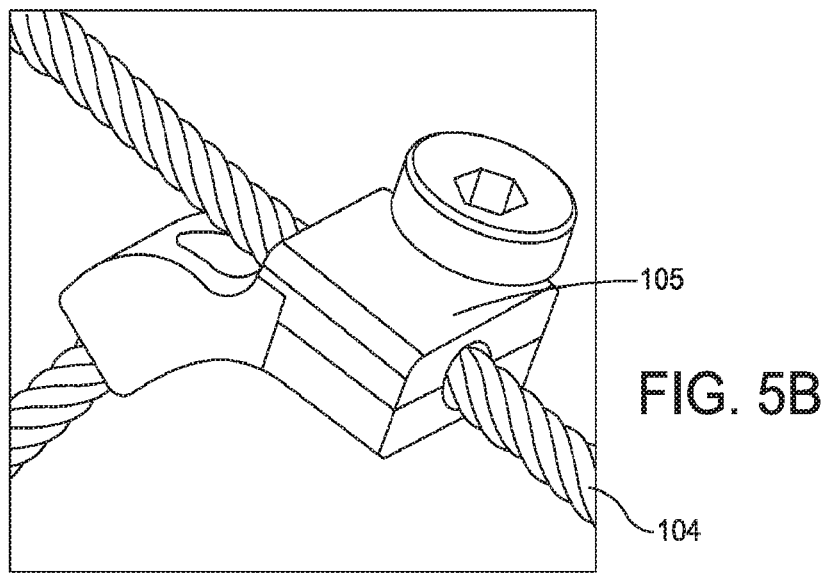

FIGS. 5A, 5B are illustrations of orthopedic tensioning cables, known in orthopedics as cerclage wiring fixtures and sometimes used to fix together fragments of fractured bone. In each case, a loop (shown only partly) is formed in a cable of stainless steel or similar cable, with an end drawn through a sliding fitting 105 that can fix the end at a point along the cable. The cable is looped through or around an anchor (not show) and coupled to the implant. The cable span is shortened and tension is applied by pulling the cable through a sliding fitting 105. In different embodiments that cable is captured by crimping the sliding fitting (FIG. 5A) or by an alternative such as more screws to close a space traversed by the cable (FIG. 5B), for holding the implant in position with appropriate tension on the cable.

Figure 6A:
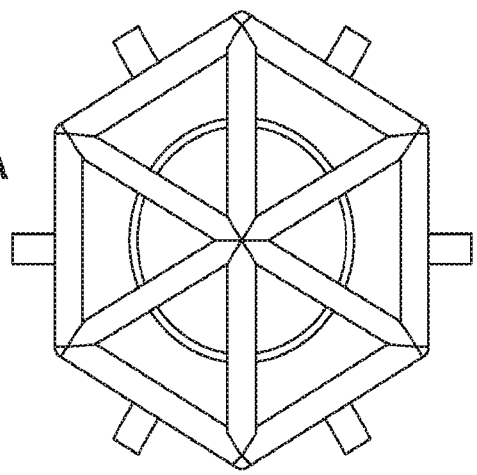
FIGS. 6A and 6B are plan and elevation views of an individual segment having an open frame structure with laterally protruding frame ends, and a regular polygon shape in plan.
Figure 6B:
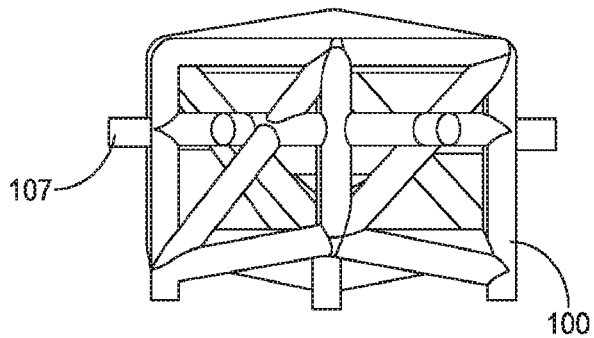
Figure 6C:
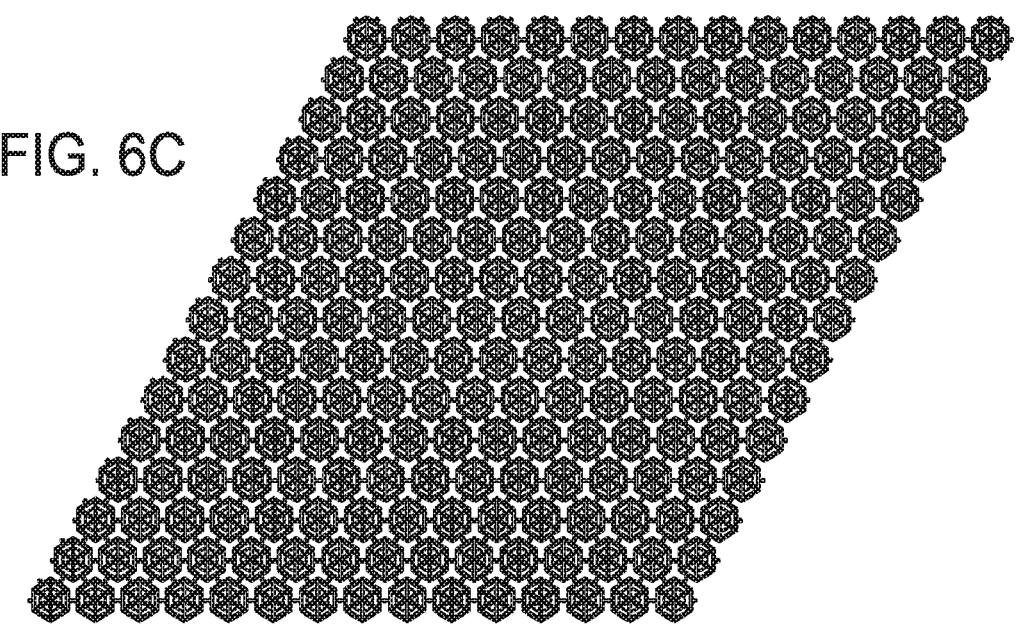
FIG. 6C is a plan view of an array of polygonal segments as in FIGS. 6A/6B, wherein the laterally protruding frame ends of adjacent segments are continuously joined in a lattice that is conformable to a nonplanar surface at least to the extent of bending of the lateral frame connections between segments.

In the embodiments of FIGS. 3A-B and 4A-C, the segments or subsets of segments are physically separate units formed as thin discs. FIGS. 6A-6C shown an embodiment where the segments 100, again using hexagons as a non-limiting example of a regular polygon shape, are attached to one another at arms 107 that span between adjacent segments (see FIG. 6C). The hexagonal bodies of the segments 100 are such that each identical segment is defined by an openwork structure of perimeter members parallel to the plane of an array of segments (FIG. 6A, 6B), standing legs generally perpendicular to the plane, and structural reinforcing struts extending diagonally.

The reinforced segment bodies are relatively rigid, but the connecting arms 107 extending between segments are relatively more flexible, allowing an array of such connected segments to form a mat or sheet as seen in FIG. 6C, which can be conformed to a curved boned surface and attached by fasteners. The openwork structure enables fasteners such as surgical staples to be passed through the segments at strategic points into underlying bone tissue. The openwork structure also advantageously can be part of a composite molded structure wherein a hydrogel sheet is molded over the segments. The segments are spaced below an exposed hydrogel surface that forms a lubricious sliding surface of the implant. The implant is supported internally by the segments and can be attached to the bone surface by fasteners passed through the segments into the bone.

In FIGS. 6A-6C the basic polygon shaped segment 100 can be made in a digital accumulation technique (3-D printing) in a metal or metal alloy comprising Ti (titanium) or Ta (tantalum), or in a polymer such as PEEK (polyetheretherketone) or a similar material for the basic polygon segment, which provided structural support. In one embodiment the segment comprises 0.25 mm diameter struts configured to define the segment, and having internal struts to provide a substantially rigid structure. The polygon segments are relatively rigid and incompressible tiles. The array of Polygons is flexible as shown in FIG. 6C. However when supplemented by one or more tension lines such as a Ti cable woven or sewn through individual polygons along an anchoring line or in a circuit, tension applied to the cable passing through the individual polygons can be arranged to pull the polygons laterally against one another, making the array substantially more rigid as installed.

Figure 7A:
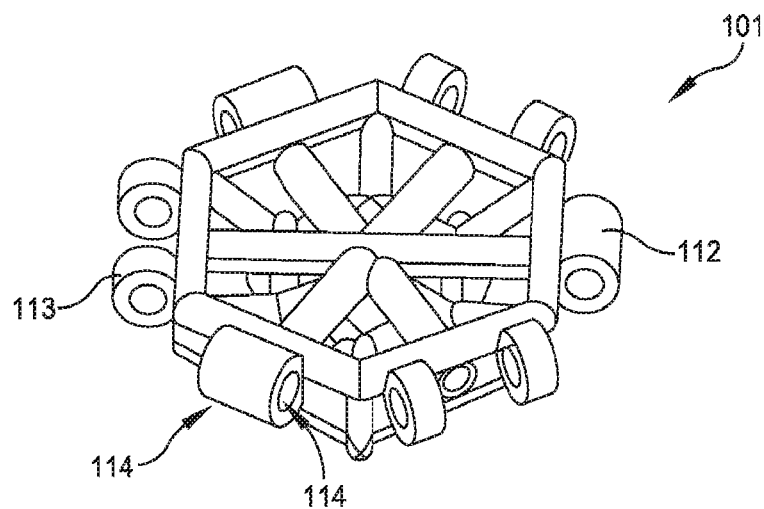
FIGS. 7A, 7B and 7C are perspective views of a polygonal segment as in FIG. 6A except with complementary alignable hinge forming elements that receive tension cables.
Figure 7B:
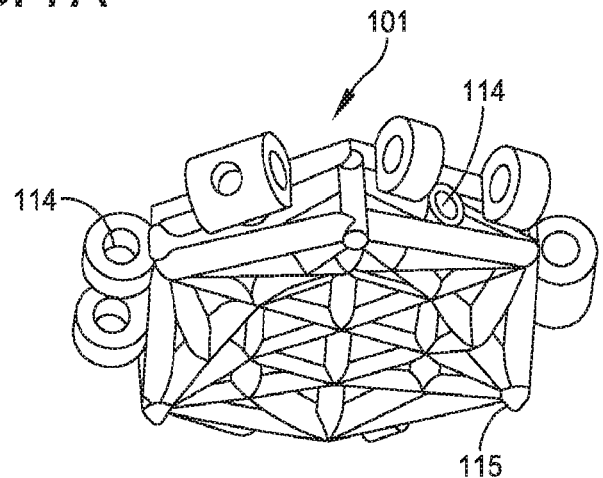
Figure 7C:
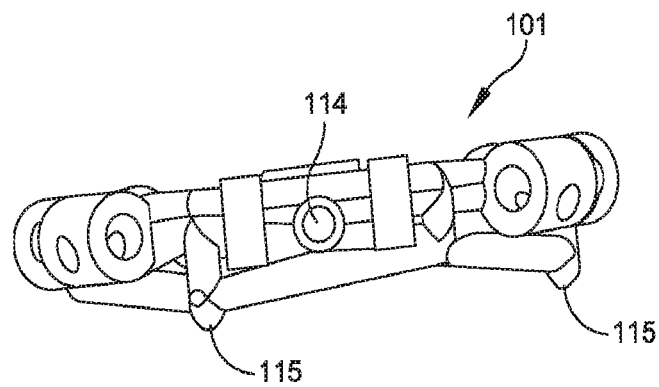
Figure 8:
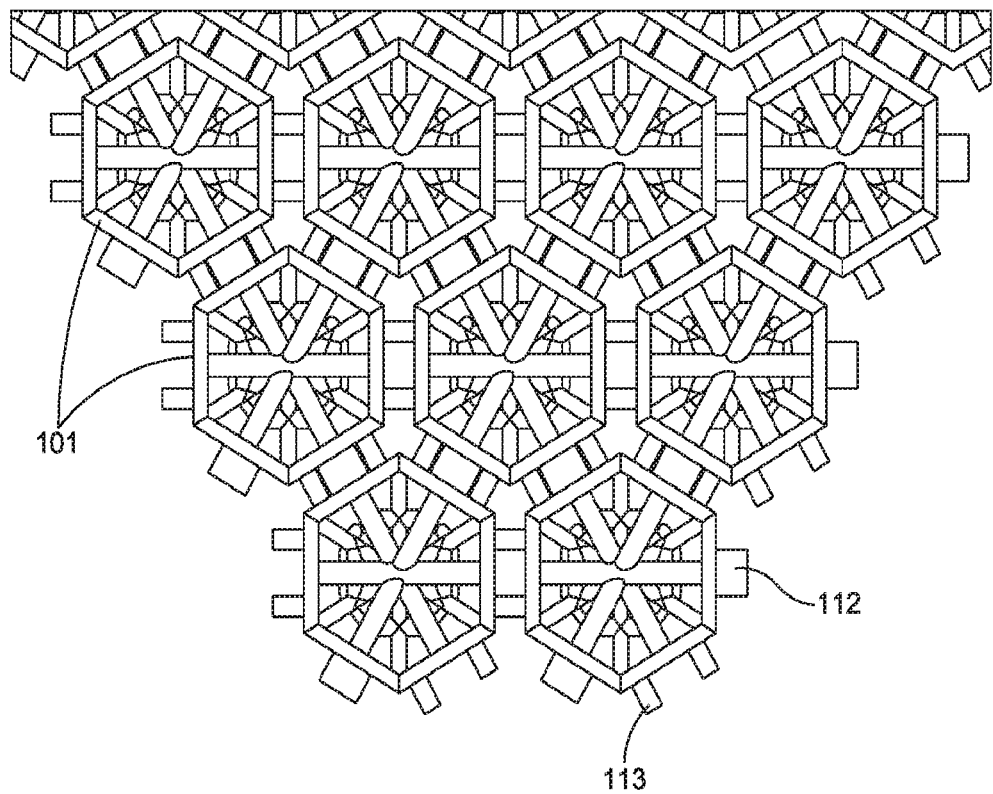
FIG. 8 is a plan view showing an array of polygonal segments with hinge forming elements in frictional engagement with one another (i.e., without inserted tension cables shown).

FIGS. 7A through 12 illustrate embodiments wherein segments that are discrete separate elements are mechanically attachable to the adjacent segments in an array, via complementary hinging structures that are provided on the edges of the segments, again represented as regular hexagon shapes as a nonlimiting example of a regular polygon. In FIGS. 7A-C, each segment 101 has an openwork structure of elongated members forming perimeter sections, standing legs and reinforcing struts. In this embodiment, each diametrically opposite side has either one central hinge knuckle 112 or two straddling hinge knuckles 113, that allow adjacent segments 101 to fit with one another in a sheet array as shown in FIG. 8. The hinge knuckles 112, 113 are cannulated or formed with bores 114, running both parallel to the associated edge of the segment and perpendicular to the associated edge. A tensioning cable 104 (not shown in FIGS. 7A-7C) can be passed through the aligned bores in the hinge knuckles 112, 113 of adjacent segments, functioning as a form of hinge pin. Additionally, tensioning cables can be passed perpendicular to the bores in the hinge knuckles, through the centers of adjacent segments.

FIGS. 7B, 7C illustrate that the underside of the segments, namely the side that will rest against a bone surface, is not flat but has a plurality of downwardly protruding points 115. The points are configured to bear against bone tissue underlying the implant, and can better accommodate surface irregularities than an alternative segment having a flat bottom surface.

Figure 9:
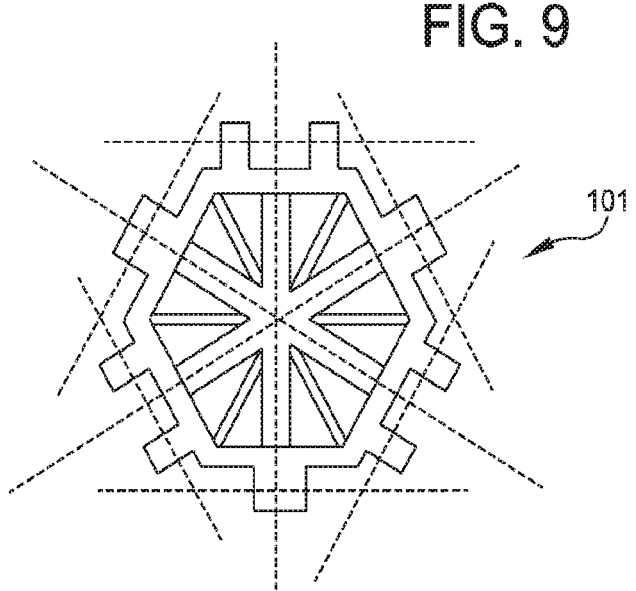
FIG. 9 is a schematic view showing one polygonal segment with hinging axes that are selectable by running a tension cable through at least two adjacent segments in the array of polygonal segments, being shown by dashed lines.

FIG. 8 is a plan view showing an array of segments that are at least temporarily attached to their adjacent segments by fitting together the hinge knuckles 112, 113 of adjacent segments. In this arrangement, a tension cable passed along a line through the cannulae of adjacent segments serves to define a hinging axis. A tension cable can be passed through the co-linear aligned cannulae of every second segment in the array, namely through the hinge knuckles and parallel to the sides of the segments. Or a tension cable can be passed through each adjacent segment in a line of segments, oriented perpendicular to the segment sides. In each case, these tension cable routes, as well as other routes and tension cable circuits, are useful to anchor the implant while enabling the implant to flex into a various potentially curving or angularly diverse shapes. In FIG. 9, the dashed lines show the potential routes of a tension cable through a segment, parallel or perpendicular to the segment sides. In an alternative embodiment (not shown Fig.), the remaining reinforcing struts shown in FIG. 9 without dashed lines, can also be cannulated to provide additional cable paths.

The embodiment of FIG. 8 can also comprise tile-like substantially rigid 3-D printed Metal, Ti, Ta or PEEK or other polymer polygon elements. The segments have cannulae 114 engineered into the structure to facilitate and guide cables coupling the array into a flexible array of individual rigid polygons. The array becomes rigid as the cables are tensioned and then crimped in tension as well as anchored. Along the edges where the cannulae of adjacent hinge knuckles are nested and in co-linear alignment, the tension line passing through the aligned cannulae of adjacent elements also defines a hinge axis. Tension applied by a tension line coupled between spaced points draws together the elements that are disposed along the tension line.

Figure 10A:
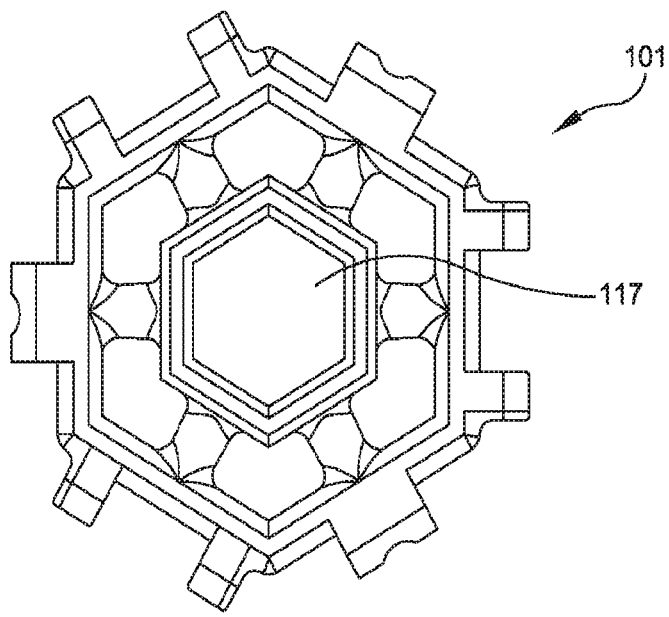
FIGS. 10A and 10B are respectively a plan view and a side elevation of an alternative segment with fewer axes than in FIG. 9, and including integrally formed protrusions on the underside of the segment for interacting with existing natural cartilage and/or bone.
Figure 10B:
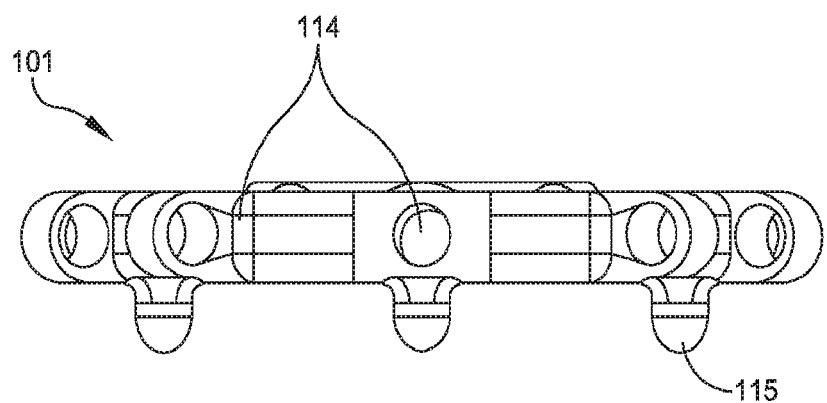

FIGS. 10A and 10B show and alternative and somewhat simplified embodiment of a regular polygon segment 101 with hinge knuckles and cannulae 114 aligned as shown in dotted lines in FIG. 9. The segment in this embodiment is one thickness of elongated members, but additionally has a central opening 117 that is useful for tension cable passage and for receiving fasteners such as surgical staples. This embodiment can likewise be made in 3-D printed Metal, Ti, Ta, PEEK or other polymer.

Figure 11:
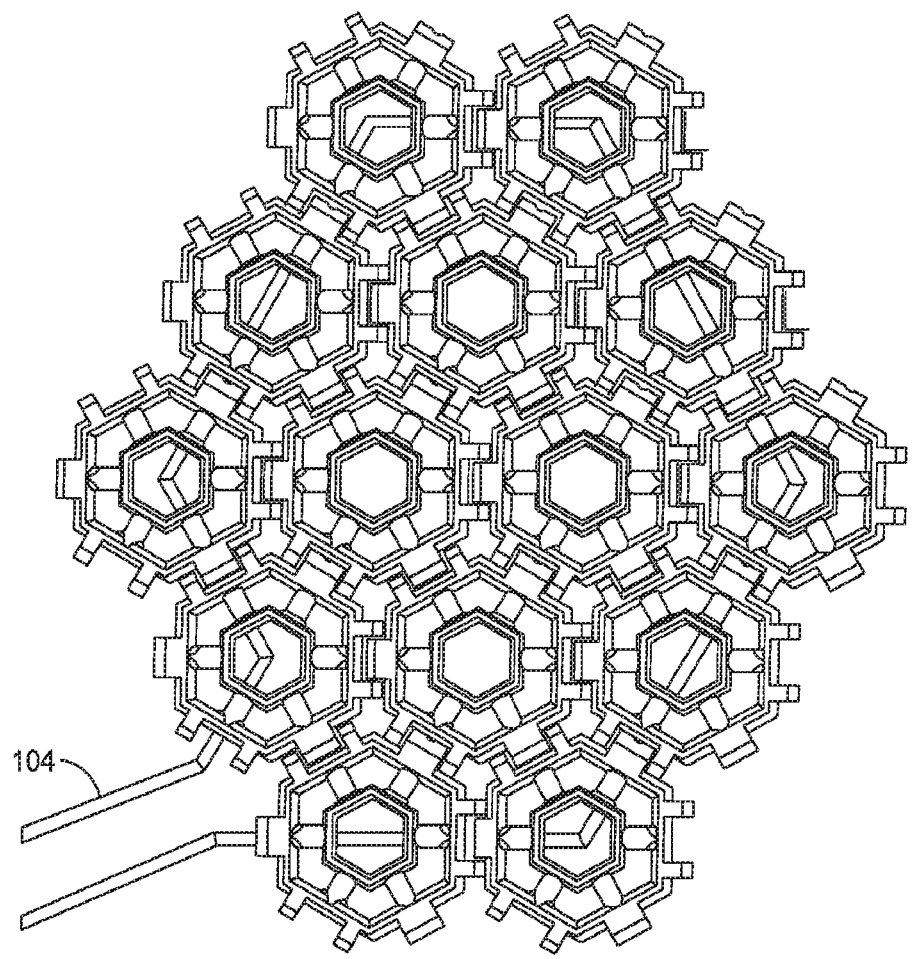
FIG. 11 is a plan view of a segment array as in FIG. 8, with a tension cable laced in a circuit through outer members of the array whereby tension on the cable draws the segments inward.

In FIG. 11, an array of simplified regular polygon segments is shown traversed by a tension cable defining a circuit through the cannulae of the segments located around the perimeter of the implant. With tension applied to the cable around the circuit, the perimeter segments are drawn inwardly against the segments occupied within the perimeter or circuit. This adds rigidity to the array of segments.

Figure 12:
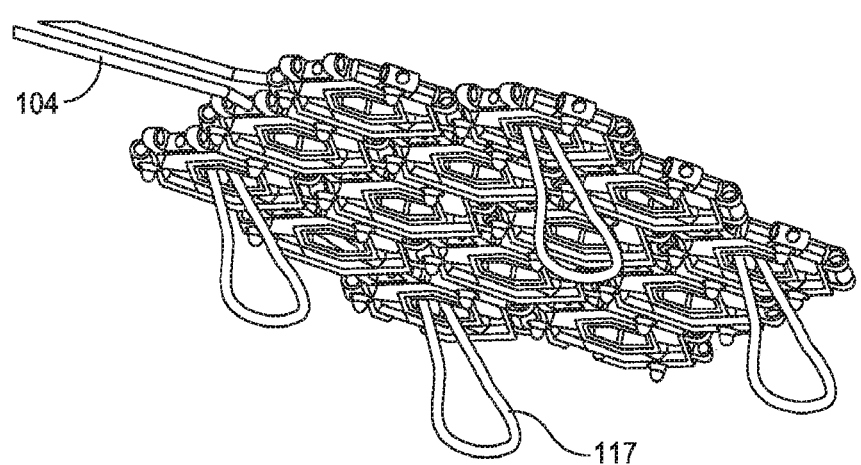
FIG. 12 is a perspective view illustrating an arrangement wherein a tension cable laced through an array include depending loops arranged to intersect or loop around fasteners (not shown) for pulling the segments of an array down onto a bone surface as well as inwardly.

A circuit as in FIG. 11 can also be configured as in FIG. 12 to engage with external fasteners (not shown) at points along the circuit. In FIG. 12, depending loops 117 can attach to anchoring staples, screws, plugs or the like. The loops 117 can be located at any of the traversed segments of the array, and thus the locations can be chosen to complement the anatomy at the recipient site, the specific shape and location of the implant and similar biomechanical demands in specific applications.

Figure 13:
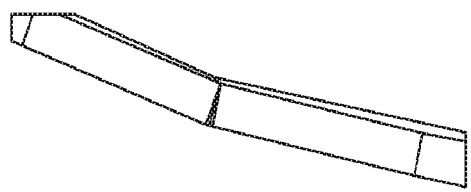
FIGS. 13 and 14 are elevation view showing adjacent segments with chamfered edge faces that when abutted form an angular diversion for accommodating part of a curved surface.

The aspect of the segments being tensions laterally against one another provides for the possibility of using inclined abutting surfaces to produce simple or complex curves in one or two planes, across an array of segments. FIG. 13 shows that inclined lateral faces forming chamfered edges on one or both of two segments that are urged against one another cause the abutting segments to diverge angularly from the common plane that they might assume if the abutting faces were parallel as in FIG. 15. Successive segments can be formed with similarly inclined side faces to follow a simple curve. By selectively interspersing sequences of plural segments with side face chambers in opposite directions, a complex curve is provided with S-shaped segments curving in opposite directions as illustrated in FIG. 14.

Figure 14:
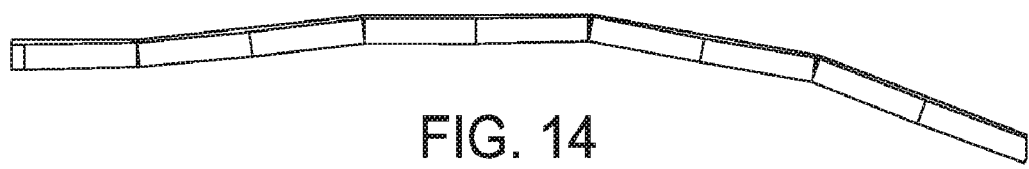
Figure 15:
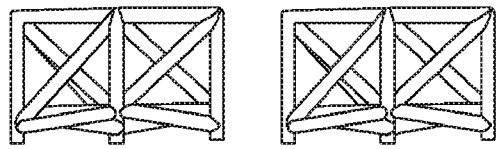
FIGS. 15-17 are illustration of segments formed of elongated members arranged as legs and struts, FIG. 16 showing an alternative for a chamfered edge and FIG. 17 showing an edge nesting structure.
Figure 16:
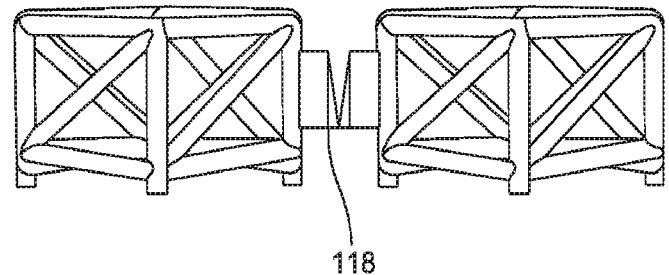
Figure 17:
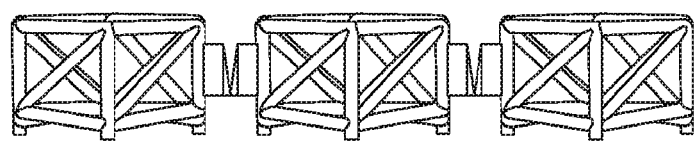

In FIGS. 13, 14, the end faces of disc-shaped segments are integrally formed with a chamfer or tilt relative to a plane perpendicular to the adjacent top and bottom faces, which in this example are parallel. FIG. 16 demonstrates that the chamfer or tilt required to achieve the same result can be obtained by inserts interspersing one or more insert elements 118 between otherwise unchamfered segments. Two mirror image inserts 118 are shown in FIG. 16. Use of one such insert would halve the angular diversion achieved. As seen in FIG. 17, similar inserts can be provided with complementary structures for locking the adjacent inserts into a predetermined alignment when urged together (in this example the abutting inserts being held in coplanar position).

The illustrated structures are 3-D modeled, enabling creation of precise geometries for the desired curvatures, which can be produced directly using 3-D printing lasers for precision fabrication, alone or together with laser or e-beam sintering of Metal, Ti, Ta, PEEK or other polymer so as to provide a desired surface configuration, or other appropriate manufacturing methods not limited to 3-D printing. The segments can be cut from a fabricated whole, or 3-D printed as individual segments assembled into a whole. Either way the segments, either cut or individually 3-D printed are engineered to restore the desired functional geometry as the threaded cable is tensioned compressing the segments into a relatively rigid structure as a whole.

The segmented implant structures disclosed herein can be advantageously formed by digital additive manufacturing techniques, i.e., 3-D printing directly into an array of segments. The implant is that case is 3-D printed as a whole, in the final anatomic shape required. Implants can be 3-D printed and then separated into segments that are supported with tension cables as discussed above. The segments can engineered and printed separately to fit together to form a flat array or a shaped structure that is complementary to an anatomical surface. Formation by 3-D printing enables the segments to be defined as individually customized segments, but 3-D printed as an assembled group. The group can include structures that engage between adjacent segments or structures that flexibly span between adjacent segments.

Figure 18A:
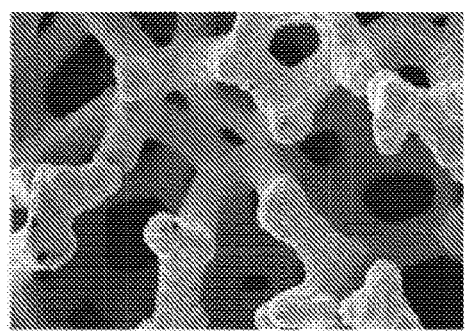
FIGS. 18A-18C show several exemplary types of trabecular and reticulated materials with porous structure that facilitate tissue ingrowth.
Figure 18B:
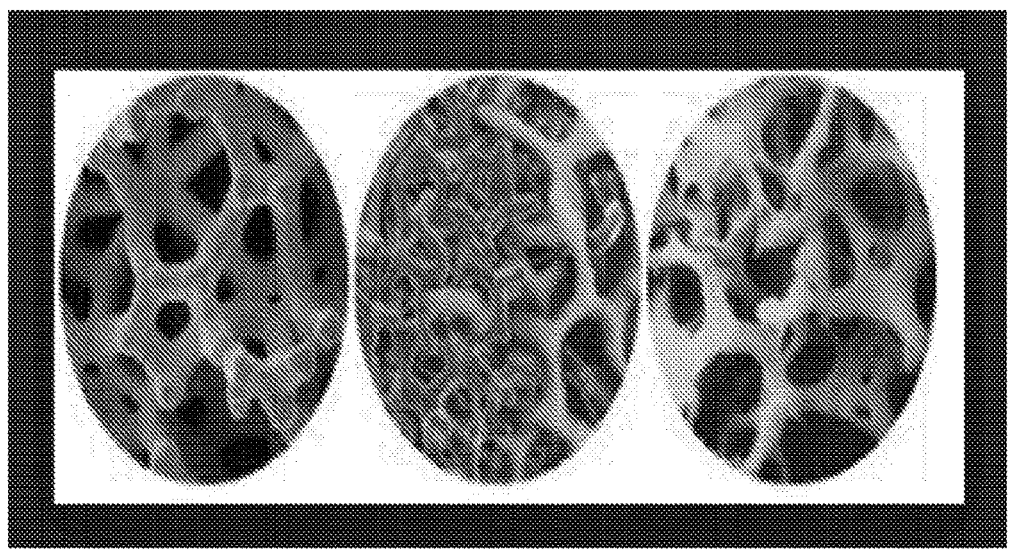
Figure 18C:
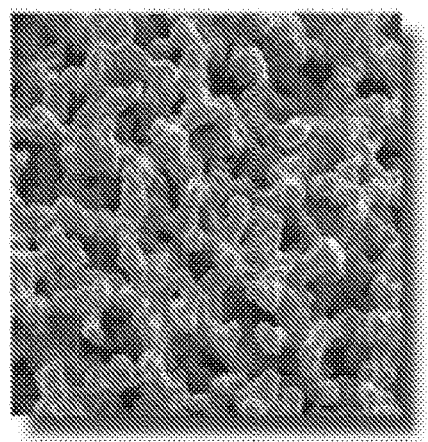

The implant segments as discussed herein are useful as the structural support within a composite molded construction that is attached to a surface of one bone in an articulating joint and carries a hydrogel layer with a lubricious sliding surface presented on a side facing an opposed bone in an articulating joint. In the embodiments of FIGS. 7C and 10B, for example, structures on the anchoring side of the implant include points that help to stabilize the position of the implant on the anchoring side (opposite from the hydrogel side). In another advantageous aspect, the anchoring side of the implant can be structured as a trabecular surface adapted to facilitate tissue ingrowth. Images of 3D-printed, FDA-approved trabecular metal available for commercial use in total joint replacements, are shown in FIGS. 18A, B and C. The specific pore size (C) can be selected to optimize bone tissue healing while facilitating hydrogel adhesion.

Figure 19A:
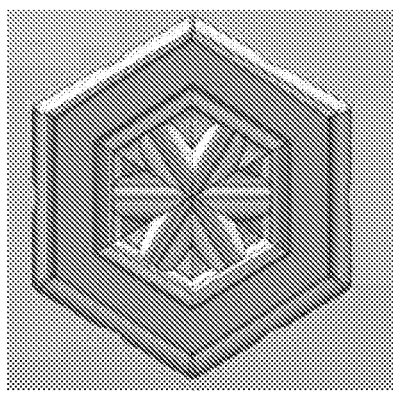
FIGS. 19A-C are plan, elevation and underside-perspective views of an alternative embodiment of a polygonal segment.
Figure 19B:
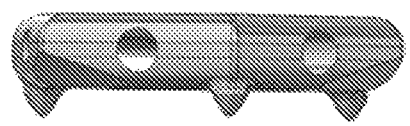
Figure 19C:
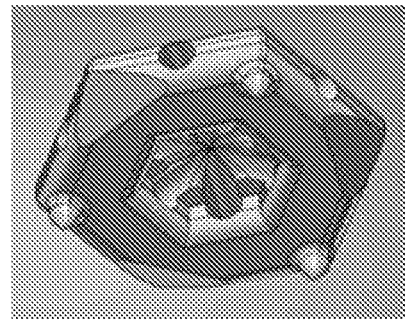
Figure 20A:
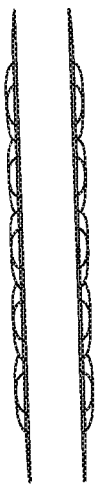
FIGS. 20A-D are elevation and perspective views showing forms of segments affixed to a backer sheet, in this case the segments comprising compressible quilted pad areas.
Figure 20B:
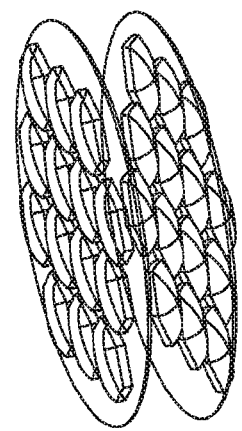
Figure 20C:
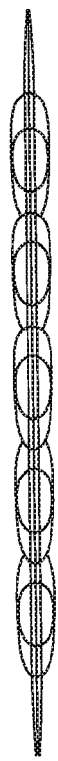
Figure 20D:
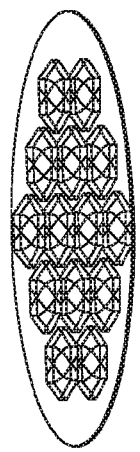

FIGS. 19A, 19B and 19C illustrate a polygonal segment 101 with cannulae through the center of the segment, and protruding points similar to those of FIGS. 7C and 10B. In the embodiment of FIGS. 19A, B, C, the underside of the segment (namely the side to be anchored against bone) has a relatively wide and flat annular area that can rest against the surface of the anchor bone. This annular area is advantageously formed of or coated with a trabecular metal layer for boney ingrowth. This embodiment has a relatively low profile and as shown in FIG. 19C has a central cavity on the underside providing access to any tensioning cable that traverses the segment through the cannulae provided. This embodiment is also preferably produced by digital additive techniques (3-D printing) in metal TI, Ta, PEEK or other polymer.

FIGS. 20A-D illustrate variations of cold pressed woven Metal, Ti or Ta wire, PEEK, or polymer mesh sheets, carrying polygonal areas adapted to be molded together with hydrogel to provide a composite structure that exposes a lubricious sliding surface to the articulating joint and facilitates attachment to and ingrowth with bone tissue on the bone to which the implant is mounted. When sandwiched together, the underside has a tightly woven mesh pressed against the bone surface layer, sintered, sewn or welded together into a quilted woven or unwoven batt mesh with lofted zones that function in a manner similar to the foregoing polygonal segments. The quilted pads or lofts facilitate hydrogel or polymer permeation to improve the sliding surface, and bonding to the woven or unwoven mesh for bone adhesion and optimal longevity of this construct.

Figure 21A:
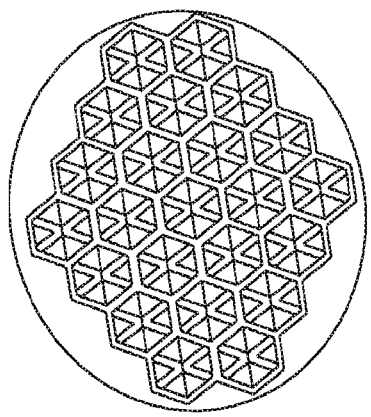
FIGS. 21A-C are detail views of a quilted pad embodiment as in FIGS. 20A-D, with FIG. 21C showing a sectional view.
Figure 21B:
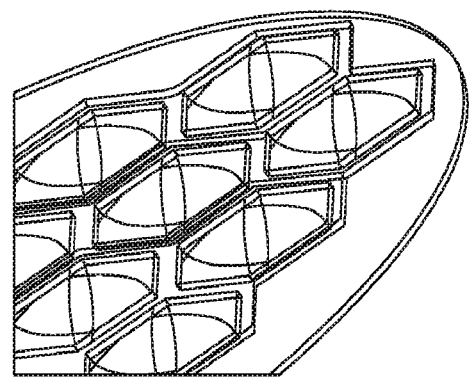
Figure 21C:
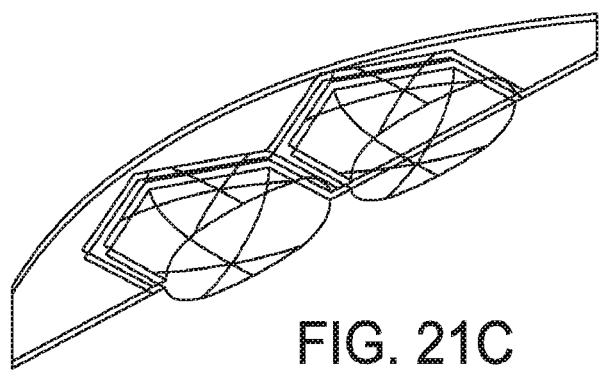

FIGS. 21A-C show a quilted woven pad (A), with a quilted structure to provide loft for hydrogel permeation, compression and tissue in-growth; a close up of a quilted structure loft (B); and a cross-section through loft of quilted woven structure (C).

Figure 22A:
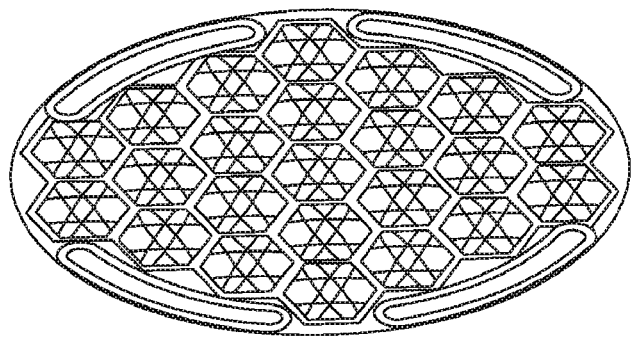
FIGS. 22A and B show additional quilted pad embodiments, wherein FIG. 22B also shows a composite molded structure having an upper exposed layer of hydrogel.
Figure 22B:
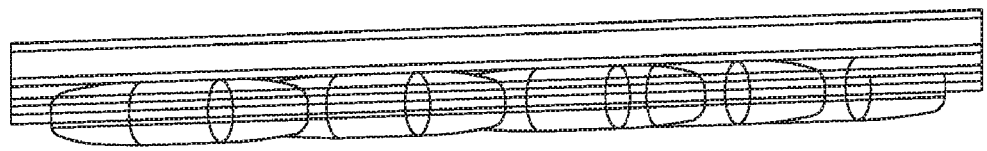

FIG. 22A shows a perspective view of the quilted-pad arrangement of sandwiched Metal, Ti, Ta, PEEK or other polymer mesh quilted material, preferable a loft or thickness equivalent to three to five times the fiber diameter to promote polymer (108) permeation and adhesion. FIG. 22B is a side section showing the quilted pads forming the underside of a composite with hydrogel occupying the upper side.

Figure 23A:
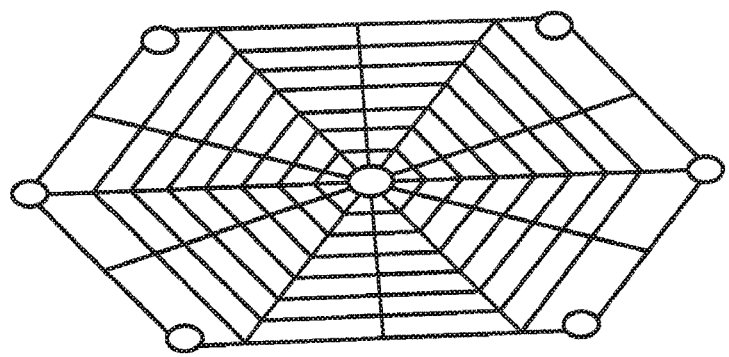
FIG. 23A shows a surgical grid that in FIG. 23B is laid over a segmented backer sheet.
Figure 23B:
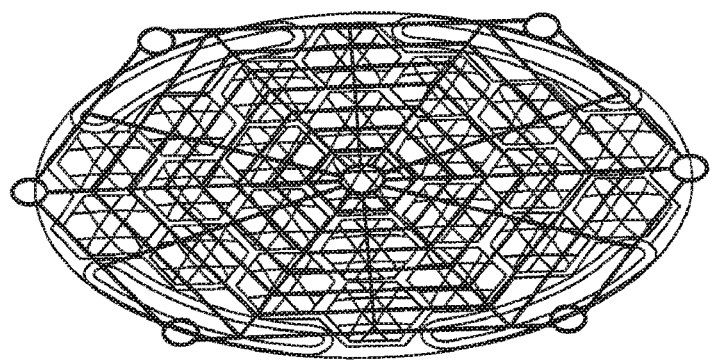
FIG. 23C show the composite molding of the backer sheet, surgical grid and hydrogel surface layer.
Figure 23C:
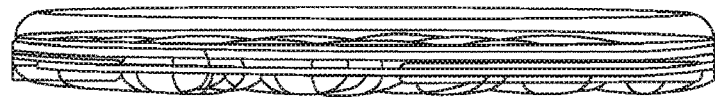

FIG. 23A shows a suture cable grid that is incorporated into the implant structure as shown in FIG. 23B prior to hydrogel composite molding. FIG. 23C show the grid including in the composite, namely between the sandwiched mesh quilt sheets. The suture cable grid spreads compressive forces urging the implant against the underlying bone surface when sutures or anchoring cables are affixed to apply tension pulling attachment points (shown as optional circles in the suture grid) away from one another and so as to wrap over bone condoyles or the like. This arrangement confines stresses to the suture grid, protecting the hydrogel interface and underlying bone ingrowth surface, while effectively compressing the quilted mesh against the bone implant interface.

Figure 24A:
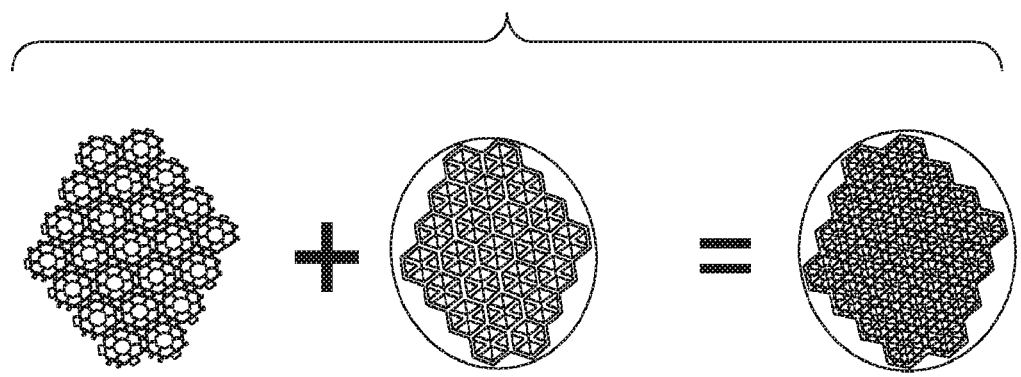
FIG. 24A is a schematic showing the stacking of a rigid-segment flexible array on a backer sheet.
Figure 24B:
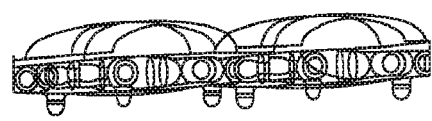
FIGS. 24B-24E are details of an embodiment wherein separate segments have domed tops and are composite molded with a hydrogel surface layer.
Figure 24C:
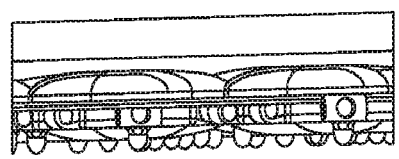
Figure 24D:
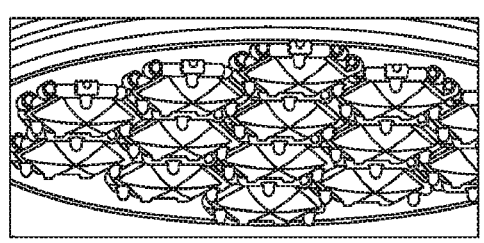
Figure 24E:
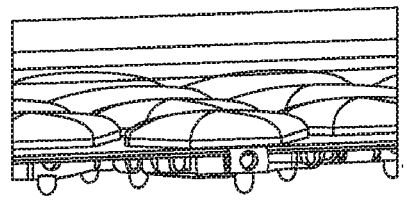

In FIG. 24A, a cannulated segment array is coupled to a woven Ti or Ta mesh sheet, creating a quilted mesh for permeation of hydrogel on one side and for adhesion of the quilted mesh to bone on the other side. It should be understood that the term "mesh" includes woven, knitted or unwoven batt structures. In FIGS. 24B, C, D and E, the segments carry quilted tops that appear as domes or bubbles into which the hydrogel is permeated.

Figure 26A:
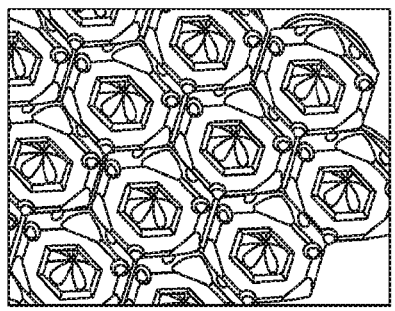
FIGS. 26A through C show a rigid-segment flexible array using segments as in FIGS. 25A-D.
Figure 26B:
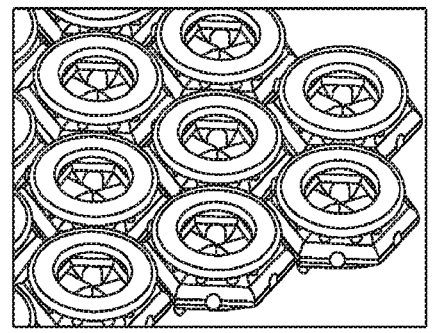
Figure 26C:
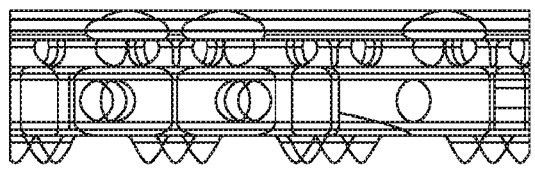
Figure 26D:
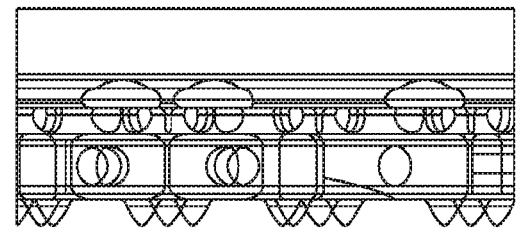
FIG. 26D is a side elevation showing a composite molding with hydrogel.

In FIGS. 25A through D, an alternative embodiment of segment 101 is shown that has a structure similar to that of FIG. 19 but with an added upper annular ring 121 and an array of macropores 122 just below the annular ring. This segment can likewise comprise a 3-D printed Metal Ti, Ta, PEEK or other polymer polygonal segment. The macropores admit hydrogel permeation and adhesion between the segments and the hydrogel. As in the embodiment of FIG. 19, tension cable holes open on the side face for receiving tension cables that traverse the segment. A central opening on the underside provides access to the cable traverse. The underside of the segment has position stabilizing points and a flat annular area that can have a trabecular structure or coating. FIGS. 26A and B respectively show an array of these segments from below and from above. FIG. 26C is a cross section through a portion of the segment array. FIG. 26D shows a composite molding in which hydrogel occupies the top surface layer.

Figure 27A:
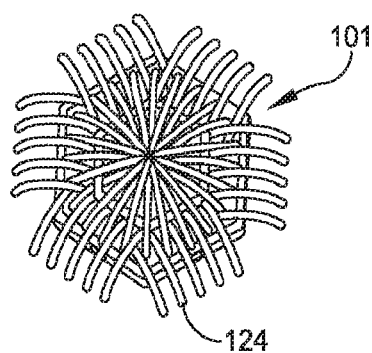
FIGS. 27A-E illustrate an alternative embodiment of rigid segments, especially for digital incremental production (3-D printing) and characterized by arching struts that flexible affix adjacent segments in FIGS. 27B-E and in FIG. 27E are embedded in the hydrogel surface layer of a composite molding.
Figure 27B:
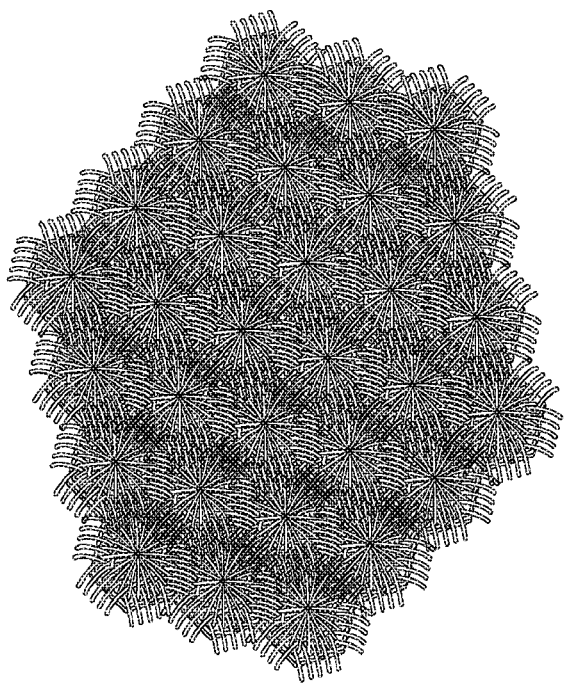
Figure 27C:
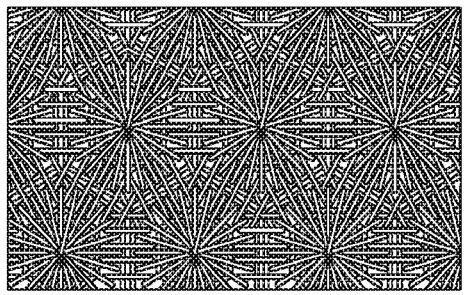
Figure 27D:
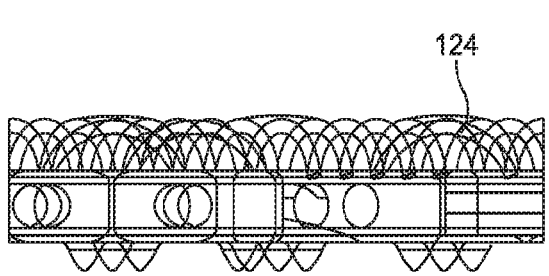
Figure 27E:
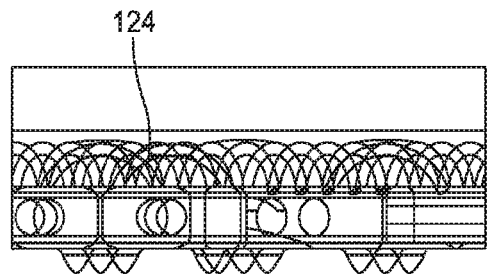

By digital additive manufacturing techniques (3-D printing), it is possible to produce an array of segments that are resiliently attached to one another as a result of the structures provided by the printing process. FIG. 27A illustrates an alternative embodiment of a polygonal segment 101 wherein arching struts 124 protrude radially from the segment. The array is printed as a unit with plural segments so formed, as shown in FIG. 27B. The arching struts of each segment are dimensioned when printed to extend over its adjacent segments at each polygonal side. Among other advantages, this resiliently attaches the adjacent segments of an array while permitting some freedom for relative displacement and angular diversion whereby the array can conform to a curved bone surface. Additionally, the cascade of arched struts from both polygonal sides at each abutment interleave with one another as shown in FIG. 27C in plan view and 27D in sectional view, providing a fibrous thickness at which hydrogel in the composite molding, shown in section in FIG. 27E, is fixed securely to the segmented anchoring system by the arching struts that become embedded in the hydrogel.

The cascading interleaved arching struts bridge across adjacent segments, creating a hinge between the rigid segments, in this case, for example, hexagons. The particular architecture of the 3-D printed structures including the arching struts can be defined by current digital additive manufacturing software to optimize for porosity, integral strut strength, and generally to provide a material modulus of elasticity gradient from the relatively rigid bone to the relatively flexible hydrogel.

As in the other embodiments, the anchoring underside of the segment can comprise or have an applied layer of trabecular Metal, Ti or Ta in a base that is relatively rigid, but carries an arcade of arching struts of a relative resilient material, especially comprising a less rigid PEEK or polymer arcade that is 3-D printed onto the metal base. In one embodiment, the arching struts are configured to emulate the tissue stiffness gradient present in a normal synovial joint at the hyaline cartilage to bone interface, namely quite stiff near the bone and progressively softer leading out toward the hydrogel sliding surface.

Figure 28A:
FIGS. 28A-B illustrate a backer sheet, for example of metal foil.
Figure 28B:
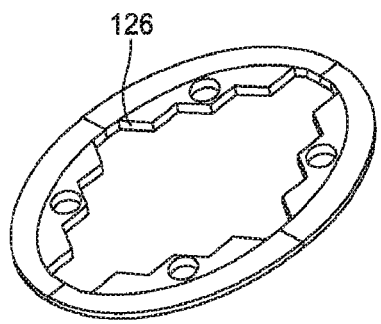

A substantially continuous foil of metal such as tantalum (Ta) or titanium (Ti) foil, or PEEK or other polymer membrane, can orient and secure multiple rigid polygonal segments of a flexible anchoring system and yet permit deformation of the foil as needed to flex, roll or fold the implant anchoring system, for delivery into the joint through a small incision, and also deformation of the foil by relative displacement of rigid segments affixed to the foil. Such an embodiment is shown in FIGS. 28A and B with segments 101 shown affixed to the surface of the foil sheet 126 in FIG. 29A. In FIG. 29B, hydrogel is molded atop the segments, permeating down to the foil layer, which stops permeation below that.

A flexible cable is strategically threaded through the rigid segments to couple the rigid segments into a construct, that can be tensioned into a rigid anchoring system with a pre-determined specific joint surface geometry for bone articular surface compression and fixation within a synovial joint. This design is disclosed as a flexible sandwiched honeycomb structure with the material property performance benefits associated with this structural design, with the additional benefit of flexibility for delivery into a restrictive space for the device's ultimate functional intent.

Figure 29A:
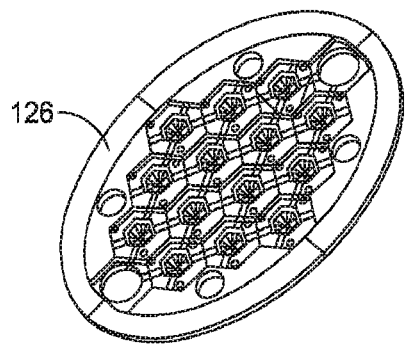
Figure 29B:
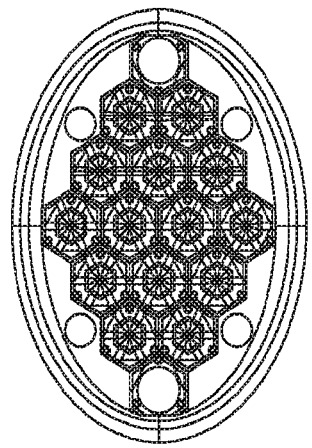
FIG. 29B shows that array and backer in a composite molding with a hydrogel surface.
Figure 30A:
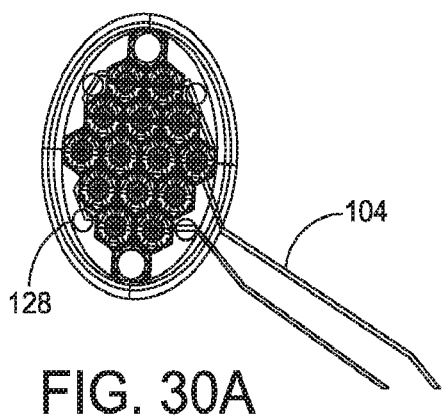
FIGS. 30A-B show an implant with a rigid-segment array on a backer sheet with a tension cable in place for cinching together and anchoring the implant.
Figure 30B:
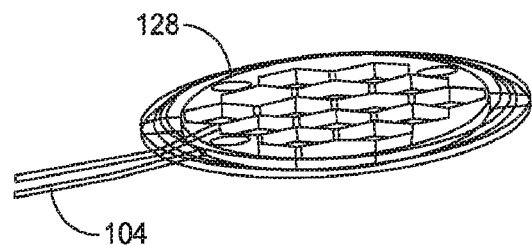
Figure 30C:
FIGS. 30C-D show an alternative embodiment with rounded perimeter segments and FIGS. 30E-F are details from FIGS. 30C-D.
Figure 30D:
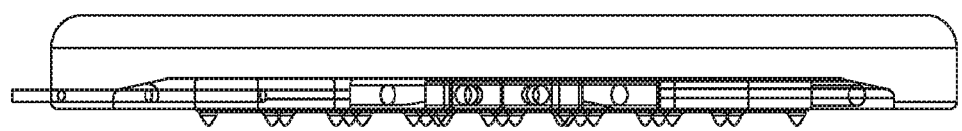
Figure 30E:
Figure 30F:
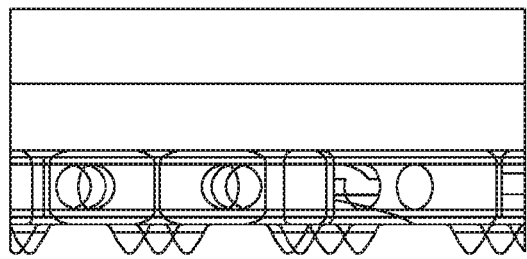

A metal, Ta, Ti foil, PEEK or other polymer membrane 126 as shown in FIG. 29A can serve as a support for 3-D printed trabecular anchor segments. The foil membrane holds the segments together, during production processes including, 3D Printing, segment cutting, threading cable, molding polymer bearing surface processes, packaging and sterilization. The foil membrane is flexible, permitting the construct to be flexed during delivery into the joint. Holes through the foil in the area of the peripheral sections can receive screw, staple or tack fixation which could be used alone or with additional provisions to locate the implant correctly and to secure the implant anchor to bone. A tension cable is laced through the segments such that when the cable is tensioned the segments get compressed into a rigid construct compressed against the bone recipient site.

FIGS. 30A through F show an embodiment with a segmented anchoring system held together with a layer of Metal, Ta, Ti foil, PEEK or other polymer membrane integral to the anchoring segments on the hydrogel side, holding the anchor segments aligned in the desired configuration for fixation of the implant. The foil is flexible, permitting deformation sufficient for delivery of the implants through a small incision (e.g., by arthroscopic access). The foil is unrolled and spread out in place, which restores the 3D structure and allows the implant to fit against and conform to the boney surface of the recipient site. Foil can function as a base layer on which the trabecular base layer is then printed, preferably with a porosity on the bone side adapted for bone tissue healing. The opposite side of the foil can serve as the base for the hydrogel bonding layer with a graduated stiffness reduction to accommodate the more compliant hydrogel, minimizing the modulus of elasticity mis-match. The foil overlying the hexagon structured layer creates a flexible sandwich honeycomb structure well known for its structural lightweight strength.

Figure 31A:
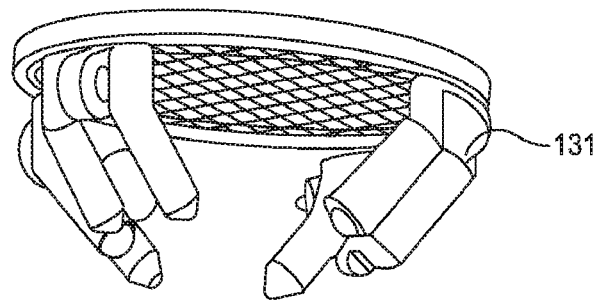
FIGS. 31A-D are perspective and plan views juxtaposing bone anchors with an implant according to the previously described embodiments.
Figure 31B:
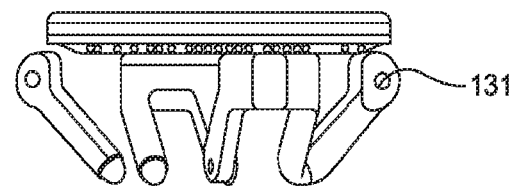
Figure 31C:
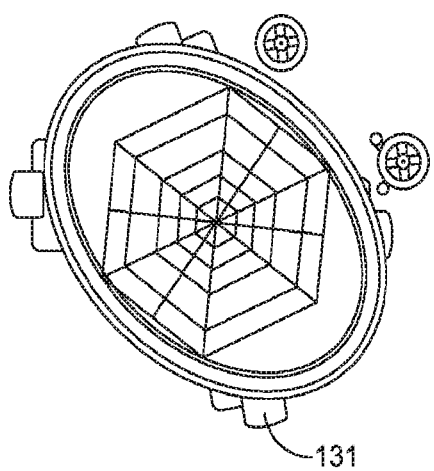
Figure 31D:
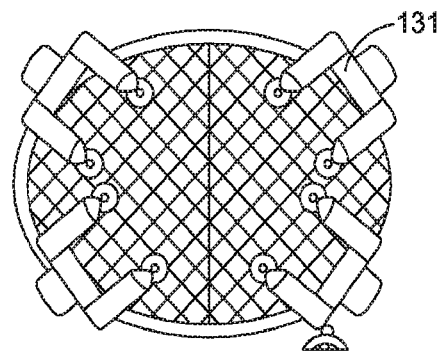

FIGS. 31A-D show juxtaposed implant and anchoring structures 131. In FIG. 31A, the anchoring structures 131 comprise driven nail-like elements or screws with eyelet heads, to be embedded in bone (not shown) around the periphery of the site at which the implant is to be attached, such as the top of the tibia. The anchors can comprise cerclage type crimping fittings at the eyelet heads such that one or more tension cables can be drawn through the eyelet and permanently fixed by crimping the eyelet. (See also FIGS. 5A, 5B.)

Figure 32:
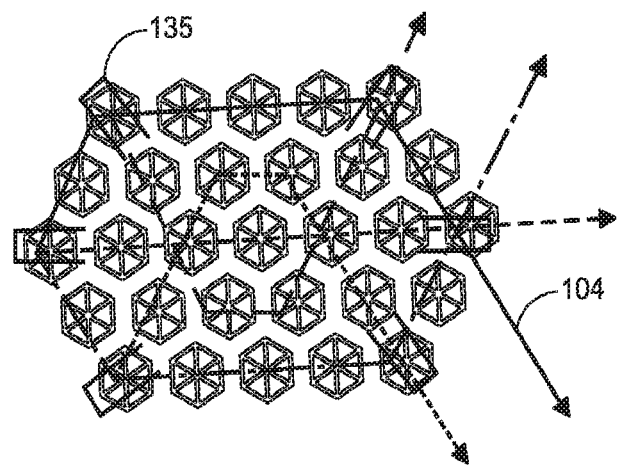
FIGS. 32-34 illustrate aspect of routing tension cables through segments of which strategically placed segments are anchored.
Figure 33:
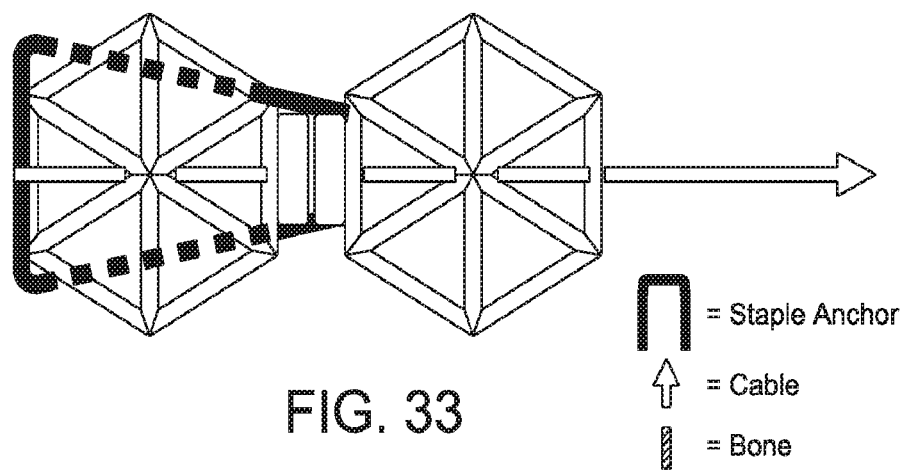
Figure 34:
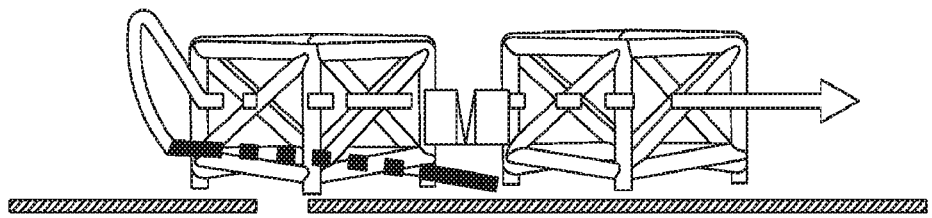

As shown in FIGS. 32-34, one or more tension cables 104 can be sewn or guided through the segments 101 in an array, along paths chosen so that tension draws the segments 101 laterally together. In FIG. 32, the arrangement of tension cables is bilaterally symmetrical and proceeds from anchoring staples 135 or from segments 101 affixed to the bone by anchoring staples 135.

In the embodiments of FIGS. 32-34, the segments are openwork hexagon segments with strut members, e.g., sized about 3-5 mm face strut dimension. This form of segment is apt to receive a staple, for example as shown in FIG. 33, because the legs of a staple can pass through spaces between the segment struts and securely engage the segment. As shown in FIGS. 33, 34, a staple can be preliminarily inserted into a segment and carried there awaiting deployment, at a position that does not protrude below the segment. When affixing the implant, the surgeon partially retracts the staple and tilts the staple up relative to the underlying bone surface. The staple then is driven down into the bone to affix that point in the array. The driven staple and/or its associated segment are then available as fixed anchoring points. Tension on the cable pulls other segments laterally toward the fixed anchoring points, stiffening the array by lateral abutment and compression of the segments, whereupon other points can be anchored in turn.

According to the embodiments disclosed herein, implants can comprise separated or laterally-attached segments that provide a downward bone interface by trabecular material or a fibrous woven or unwoven mesh, and are molded in a composite structure with a hydrogel surface layer. The lateral attachment can comprise a sheet or foil that carries the segments into position as well as providing a barrier to prevent permeation of the hydrogel into the fibrous or trabecular layer on the underside.

Trabecular Bone interface struts thickened for optimal pore size for tissue healing, while accommodating cables, cannulae, staple slot and staples (see below). For intrusion or permeation of hydrogel into the segments, in the foregoing embodiments, a fibrous mesh or batt underlies the segments to form a permeation barrier at the underside (the bone affixation side). The hydrogel is molded into a perforated or fibrous structure for secure attachment of the hydrogel to the segments, such as a dome with lateral macropores or an array of arching struts. A smooth anchor-bearing surface interface can be provided with bearing surface on-lay.

The paths traversed by tension cables are arranged with clearance and separation so that multiple cables can pass thru single polygon segments when necessary. Cannulae and/or dividers prevent cable overlap and binding by providing a defined path.

The perimeter polygons will be anatomic joint implant specific with modified outside edges "rounded" to minimize stress at the gel-polygon interface at corner edges and to facilitate outer edge adhesion of hydrogel for implant edge coverage.

At least certain ones of the perimeter polygons in an array preferably are securely compressed to the subchondral bone surface along entire margin of implant. This may be facilitated, for example, using bone anchors that engage with perimeter polygons or are a least located closely adjacent to the perimeter polygons. The perimeter polygons selected for anchoring can be at regularly spaced points, at apices of an array or otherwise strategically placed to maximize compression of the array against the subchondral bone tissue (including but not limited to any anchor polygons that are affected by a nearby or polygon-traversing bone anchor).

Rim/Perimeter Anchor Polygons preferably meet some or all of the above design criteria. In addition, Anchor Polygons can be particularly configured to accommodate the cable stress loads through cannulae or plate partitions controlling the path of cable to and/or from a bone Anchor.

Staple Anchor Polygons accommodate the cable and define staple slots or paths by which a staple or similar fastener can pin one or more anchor polygons to the subchondral bone tissue. One option is to supply or package the Staple in a semi-retracted "Neutral" slot position at which the Staple is poised to be driven for delivery into the bone of the joint, e.g., by applying manual force using a tool. The staple can be engaged into a "deployed" slot position once the array of elements is positioned on the joint surface, over a prepared area including Staple bone entry sites. Staples can be manipulated (moved, set, retracted, etc.) with an Arthroscopic suture grabber by catching an edge of a staple (or a cable loop) and pushing/pulling backwards. Manipulation can be used to move the staple back in the "Neutral" slot and for levering the back edge of Staple up until it securely engages the "Deployed" slot, aligning staple prong tips into subchondral bone while the body of the staple engages in the array element. "Neutral" and "Deployed" slots can be provided at a 45-60° angle to each other. The staple is driven into & below subchondral bone, along the deployed slot until locked into place. The staple final locked position couples the segment/polygon and the staple as a solid unit engaging the subchondral articular surface under wedge compression and cable tension.

The following outline details surgical steps in installing an implant as described:

I. Prepare Recipient Site
  A. Size/Template & Mark Recipient Site
  B. Debride/Remove residual Cartilage
  C. Contour Recipient Site Bone Surface D. Template & Mark Staple Recipient Sites
II. Align Staple Anchor Fixation Sites
A. Adjust Implant Trial Staple Recipient Sites
B. Prepare Aligned Staple Anchoring Sites
C. Install Screws if Screw Anchor Utilized
D. Evacuate All Joint Debris
III. Install & Secure Implant
A. Deliver Implant into Joint (Compressive Cannula)
B. Adjust Implant Rim Position & Staple Alignment
C. Align & Deploy "Remote" Posterior Staple Anchors
D. Secure, Tighten & Lock "Remote" Posterior Anchors & Tension Cable
E. Align & Deploy "Near" Anterior Staple Anchors
F. Secure, Tighten & Lock "Near" Anterior Anchors & Tension Cable
G. Tighten & Lock Cable Tension
H. Evacuate All Joint Debris Short and long-term clinical design considerations are to achieve goals including a) pain relief; b) restoration of patient function; c) minimal morbidity; d) stable fixation to permit tissue ingrowth; e) Rigid fixation necessary for bone ingrowth; e) Stable, less rigid, fixation necessary for fibrous tissue ingrowth; f) Device material properties at tissue implant interface must reflect rigidity demands of recipient site and desired tissue ingrowth.

As described herein, an implant for emulating hyaline cartilage in an articulating mammalian joint includes an array of laterally adjacent segments encompassing an area of a surface corresponding to the hyaline cartilage, and a hydrogel layer affixed to at least on one side of the implant, configured to provide an exposed sliding surface in the articulating joint. Specifically, the segments are movable relative to one another to a limited extent enabling segments in the array to diverge from one another and to conform to a topography to which the implant is to be attached.

The segments are relatively displaceable in at least one of lateral inter-spacing and inclination relative to one another so as to diverge from a direct abutment in a common plane. In certain embodiments, the segments define cannulae through which at least one line can be passed to couple adjacent ones of at least a subset of the segments. In additional embodiments, a mechanically attached subset of adjacent ones of the segments are configured to hinge relative to one another on at least one axis defined by cannulae through which the line passes.

Advantageously, the segments define aligned cannulae along a plurality of parallel lines through which a tension line can be passed defining hinge axes. For cinching together adjacent segments in at least a subset of the array, an outer one of the plural tension lines surrounds an inner one of the tension lines, and the outer and inner ones of the tension lines are tensioned separately whereby a complex curved shape can be assumed.

In some embodiments, the segments comprise regular polygon shapes having complementary hinge forming edge structures at which adjacent segments hingeably engage. These can have cannulated hinge knuckles, arching struts and other shapes that engage discrete segments. Alternatively or additionally, the segments can be affixed to a backer sheet of fiber or foil that provides a barrier to hydrogel permeation in a composite molding, or can carry a trabecular or similar material configured for tissue ingrowth.

Certain embodiments of the segments are structured to admit a fastener for affixing selected ones of the segments to underlying tissue. For example, segments comprising vertical, horizontal and inclined frame members can receive staples or similar fasteners configured to extend between spaced ones of the frame members for affixing the segment to a bone underlayment.

The invention having been disclosed in connection with several examples and illustrative embodiments, it should be noted that the invention is not limited to the embodiments used as examples, and is capable of other embodiments within the scope of the appended claims defining the scope of the invention in which exclusive rights are claimed.

The invention claimed is:

1. An implant for emulating hyaline cartilage in an articulating mammalian joint, the implant comprising:
   an array of laterally adjacent segments encompassing an area of a surface corresponding to the hyaline cartilage;
   a hydrogel layer affixed to at least one side of the implant, configured to provide an exposed sliding surface in the articulating joint;
   at least some of the segments are movable relative to one another, such that in an expanded position at least some of the segments are entirely spaced apart from an adjacent one of the segments by a gap, and
   a size of the gap between of the segments is adjustable to enable the segments to converge toward or diverge from one another and to conform to a topography to which the implant is to be attached.

2. The implant of claim 1, wherein the segments are displaceable in at least one of lateral inter-spacing and inclination relative to one another.

3. The implant of claim 2, wherein the segments define cannulae and further comprising at least one line passing through the cannulae of adjacent ones of at least a subset of the segments.

4. The implant of claim 3, wherein at least a mechanically attached subset of adjacent ones of the segments are configured to hinge relative to one another on at least one axis defined by cannulae through which the line passes.

5. The implant of claim 2, wherein the segments define aligned cannulae along a plurality of parallel lines and further comprising at least one line passing through the cannulae and defining hinge axes.

6. The implant of claim 3, comprising a plurality of lines passing through the cannulae of adjacent ones of a tethered subset of the segments, and wherein an outer one of the lines surrounds an inner one of the lines and the outer and inner ones of the lines are tensioned separately.

7. The implant of claim 1, wherein the segments comprise regular polygon shapes having complementary hinge forming edge structures at which adjacent segments hingeably engage.

8. The implant of claim 7, wherein the hinge forming edge structures are cannulated along at least one of an axis of hingeable engagement and an axis extending through an associated one of the regular polygon shapes.

9. The implant of claim 1, wherein the segments include a backer layer configured for tissue ingrowth.

10. The implant of claim 1, wherein the segments are structured to admit a fastener for affixing selected ones of the segments to underlying tissue.

11. The implant of claim 10, wherein the segments comprise vertical, horizontal and inclined frame member, and wherein at least one said fastener is configured to extend between spaced ones of the frame members.

12. The implant of claim 11, wherein the fastener comprises a staple and is configured for selective placement at one of at least two different angles relative to the frame members.

13. The implant of claim 12, wherein the staple is configured to extend through the frame members at a selected on of at least two angles relative to an underlying surface.

14. The implant of claim 11, wherein at least one of the frame members and the fastener is configured for attachment of a suture.

15. The implant of claim 1, wherein at least one of the laterally adjacent segments and subsets of the laterally adjacent segments are displaceable relative to one another at lines of abutment.

16. The implant of claim 15, wherein said at least one of the laterally adjacent segments and subsets of the laterally adjacent segments are configured to diverge angularly along the lines of abutment, whereby the implant can conform to a surface that has a changing gradient across the lines of abutment.

17. The implant of claim 1, further comprising a tensioning element configured to engage laterally adjacent segments to adjust the size of the gap.

18. The implant of claim 17, wherein the tensioning element drives the laterally adjacent segments into contact with each other and out of contact with each other.

\* \* \* \* \*

UNITED STATES PATENT AND TRADEMARK OFFICE
CERTIFICATE OF CORRECTION

PATENT NO. : 10,485,664 B2
APPLICATION NO. : 15/542352
DATED : November 26, 2019
INVENTOR(S) : Kevin A. Mansmann and Edward J. Cheal It is certified that error appears in the above-identified patent and that said Letters Patent is hereby corrected as shown below:

In the Claims

In Claim 1, at Column 20, Line 23, after the word "between", delete the word "of".

Signed and Sealed this
Thirty-first Day of March, 2020

Andrei Iancu
*Director of the United States Patent and Trademark Office*